United States Patent [19]

O'Keefe

[11] 4,146,437

[45] Mar. 27, 1979

[54] METHOD FOR EVALUATING A SYSTEM FOR ELECTRODEPOSITION OF METALS

[75] Inventor: Thomas J. O'Keefe, Rolla, Mo.

[73] Assignee: The Curators of the University of Missouri, Columbia, Mo.

[21] Appl. No.: 831,811

[22] Filed: Sep. 9, 1977

Related U.S. Application Data

[63] Continuation of Ser. No. 645,609, Dec. 31, 1975, abandoned.

[51] Int. Cl.² ............................................. G01N 27/46
[52] U.S. Cl. ................................ 204/1 T; 204/195 R; 204/14 R
[58] Field of Search .................. 204/1 T, 14 R, 195 R

[56] References Cited

U.S. PATENT DOCUMENTS 3,925,168  12/1975  Costas ................................... 204/1 T

OTHER PUBLICATIONS

Adams, "Electrochemistry at Solid Electrodes", New York, Marcel Dekker, Inc., 1969, pp. 122-159.
Willard et al., "Instrumental Methods of Analysis", Med., 1974, pp. 652 & 653.
Mantell et al., "Transactions of the Metallurgical Society of AIME", vol. 236, May 1966, pp. 718-725.
Vennesland et al., "Acta Chemica Scandinavica", vol. 27, 1973, No. 3, pp. 846-850.

Primary Examiner—T. Tung
Attorney, Agent, or Firm—Koenig, Senniger, Powers and Leavitt

[57] ABSTRACT

A method is provided for evaluating an unknown electrolytic system comprising an electrolytic solution and electrodes for electrodeposition of metal with respect to determining the performance characteristics of the electrolytic solution, detection of impurities and additives in the electrolytic solution, estimation of the current efficiency characteristics of the system, or determining the performance characteristics of an electrode. An electrolytic circuit is established comprising a sample of the electrolytic solution for the system, two electrodes immersed in the solution and spaced from one another therein, and a variable and reversible voltage source having its output terminals respectively connected to the electrodes. A predetermined initial voltage is applied to one of the electrodes constituting a working electrode. Thereafter, the voltage is varied in the negative direction until a predetermined cathodic current or predetermined maximum voltage sufficient to cause a cathodic reaction is attained at the working electrode. The direction of the voltage change is then reversed and the voltage is varied in the positive direction until a predetermined minimum voltage or a predetermined minimum current is attained at the working electrode. This process is repeated through a plurality of cycles and the current obtained is recorded as a function of voltage for a selected cycle. The performance characteristics of the sample solution, the presence of an impurity or additive, the current efficiency, or the working electrode characteristics are determined according to the recorded relationship between current and voltage. This method is useful in the control of electrodeposition processes since it not only provides a basis for evaluating electrolytic solutions and electrodes but further constitutes an analytical tool adapted for determining compositional adjustments necessary for optimum cell performance.

20 Claims, 19 Drawing Figures

SCHEMATIC FOR APPARATUS SET-UP

Cyclic voltammogram for acidified zinc sulfate electrolyte (0.77M $Zn^{++}$, 1M $H_2SO_4$). A, starting potential; B, decomposition potential; C, reversing potential; D, crossover; E, potential of maximum anodic current. Area of aluminum cathode = 1.18 $cm^2$.

Schematic for apparatus set-up

CYCLIC VOLTAMMOGRAM FOR ACIDIFIED ZINC SULFATE ELECTROLYTE (0.77 M $Zn^{++}$, 1 M $H_2SO_4$) CONTAINING 40 PPM GLUE. AREA OF ALUMINUM CATHODE = 1.18 $cm^2$.

CYCLIC VOLTAMMOGRAM FOR ACIDIFIED ZINC SULFATE ELECTROLYTE (0.77 M $Zn^{++}$, 1 M $H_2SO_4$) CONTAINING 40 ppb Sb. AREA OF ALUMINUM CATHODE = 1.18 $cm^2$.

CYCLIC VOLTAMMOGRAM FOR ACIDIFIED ZINC SULFATE ELECTROLYTE (0.77 M $Zn^{++}$, 1 M $H_2SO_4$) CONTAINING 40 ppb Sb - 20 ppm GLUE. AREA OF ALUMINUM CATHODE = 1.18 $cm^2$.

POLARIZATION CURVES FOR ABC PORTION OF VOLTAMMOGRAM FOR ACIDIFIED ZINC SULFATE ELECTROLYTE (0.77 M $Zn^{++}$, 1 M $H_2SO_4$), a, NO ADDITIONS; b, 10 ppm GLUE; c, 20 ppm GLUE; d, 40 ppm GLUE; e, 10 ppb Sb; f, 20 ppb Sb; g, 40 ppb Sb; h, 40 ppb Sb - 20 ppm GLUE. AREA OF CATHODE = 1.18 $cm^2$.

POLARIZATION CURVES FOR EXPANDED CD PORTION OF VOLTAMMOGRAM PURE ACIDIFIED ZINC SULFATE ELECTROLYTE (0.77 M $Zn^{++}$, 1 M $H_2SO_4$). a, NO ADDITIONS AND 10 ppb Sb; b, 10 ppm GLUE; c, 40 ppm GLUE. AREA OF ALUMINUM CATHODE = 1.18 $cm^2$.

EFFECT OF SWEEP RATE ON THE CATHODIC POLARIZATION CURVE (PORTION ABC) FOR ACIDIFIED ZINC SULFATE ELECTROLYTE. a, 1 mV/SEC; b, 5 mV/SEC; c, 10 mV/SEC; d, 50 mV/SEC; e, 100 mV/SEC. AREA OF ALUMINUM CATHODE = 1.18 cm².

CYCLIC VOLTAMMOGRAM FOR ACIDIFIED ZINC SULFATE ELECTROLYTE (0.77 M $Zn^{++}$, 1 M $H_2SO_4$) CONTAINING 2 ppm Cu. AREA OF ALUMINUM CATHODE = 1.18 $cm^2$.

ANODIC SWEEP CURVES FOR UNADULTERATED, GLUE OR CHLORIDE ION CONTAINING ACIDIFIED COPPER SULFATE ELECTROLYTE (45 gpl $Cu^{++}$, 200 gpl $H_2SO_4$) AT 40 AND 60°C. AREA COPPER CATHODE = 1.26 $cm^2$. SCAN RATE = 1 MV/SEC.

ANODIC SWEEP CURVES FOR ACIDIFIED COPPER
SULFATE ELECTROLYTE (45 gpl $Cu^{++}$, 200 gpl
$H_2SO_4$) AT 30 AND 60°C CONTAINING 10, 25, 50
OR 100 mg/l GLUE. AREA OF COPPER CATHODE =
1.26 $cm^2$. SCAN RATE = 1 mV/SEC.

ANODIC SWEEP CURVES FOR UNADULTERATED OR ORGANIC ADDITIVE CONTAINING ACIDIFIED COPPER SULFATE ELECTROLYTE (45 gpl $Cu^{++}$, 200 gpl $H_2SO_4$) AT 40 AND 60°C. AREA OF COPPER CATHODE = 1.26 $cm^2$. SCAN RATE = 1 mV/SEC.

CATHODIC SWEEP CURVES FOR UNADULTERATED OR THIOUREA CONTAINING ACIDIFIED COPPER SULFATE ELECTROLYTE (45 gpl Cu$^{++}$, 200 gpl H$_2$SO$_4$) AT 40 AND 60°C. AREA OF COPPER CATHODE = 1.26 cm$^2$. SCAN RATE = 1 mV/SEC.

VOLTAMMOGRAM FOR ACIDIFIED COPPER SULFATE ELECTROLYTE (45 gpl $Cu^{++}$, 200 gpl $H_2SO_4$) AT 30, 40, 50 AND 60°C. AREA OF TITANIUM CATHODE = 0.5 cm². SCAN RATE = 1 mV/SEC.

VOLTAMMOGRAM FOR ACIDIFIED COPPER SULFATE ELECTROLYTE (45 gpl $Cu^{++}$, 200 gpl $H_2SO_4$) AT 40°C CONTAINING 25 mg/l CHLORIDE ION. AREA OF TITANIUM CATHODE = 0.5 cm². SCAN RATE = 1 mV/SEC.

VOLTAMMOGRAM FOR ACIDIFIED COPPER SULFATE ELECTROLYTE (45 gpl $Cu^{++}$ 200 gpl $H_2SO_4$) AT 40°C CONTAINING 50 mg/l GLUE. AREA OF TITANIUM CATHODE = 0.5 $cm^2$. SCAN RATE = 1 mV/SEC.

VOLTAMMOGRAM FOR ACIDIFIED COPPER SULFATE ELECTROLYTE (45 gpl $Cu^{++}$ 200 gpl $H_2SO_4$) AT 40°C CONTAINING 50 mg/l SEPARAN (DOW NP-10). AREA OF TITANIUM CATHODE = 0.5 $cm^2$. SCAN RATE = 1 mV/SEC.

VOLTAMMOGRAM FOR ACIDIFIED COPPER SULFATE ELECTROLYTE (45 gpl $Cu^{++}$, 200 gpl $H_2SO_4$) AT 40°C CONTAINING 25 mg/l THIOUREA. AREA OF TITANIUM CATHODE = 0.5 cm². SCAN RATE = 1 mV/SEC.

VOLTAMMOGRAM FOR ACIDIFIED COPPER ELECTROLYTE (45 gpl $Cu^{++}$, 200 gpl $H_2SO_4$) AT 50°C CONTAINING 50 mg/l THIOUREA. AREA OF TITANIUM CATHODE = 0.5 cm². SCAN RATE = 1 mV/SEC.

METHOD FOR EVALUATING A SYSTEM FOR ELECTRODEPOSITION OF METALS

This is a continuation of application Ser. No. 645,609, filed Dec. 31, 1975, now abandoned.

BACKGROUND OF THE INVENTION

This invention relates to the field of the electrolytic deposition of metals and, more particularly, to an improved method of evaluating electrolytic systems with respect to the detection of impurities in the electrolytic solution of such systems, the current efficiency characteristics of the solution and the characteristics of electrodes and electrode materials of the systems.

The electrolytic deposition of metals finds extensive commercial use in a variety of applications. Certain metals such as zinc and copper are often recovered by electrowinning techniques in which a solution obtained by leaching an ore concentrate with sulfuric acid is subjected to electrolysis, with resultant deposition of the metal at the electrolytic cathode. Additionally, metals which have been recovered in crude form from ores by pyrometallurgical techniques are in some instances refined electrolytically. Thus, copper produced by conventional smelting and converter processes is purified by dissolving it in sulfuric acid and electrolytically depositing it on a cathode with attendant concentration of nickel and noble metals in the electrolytic solution or a precipitated sludge. The electrodeposition of the metals finds further extensive use in the application of protective or decorative metal platings such as chromium, nickel, silver and gold.

In certain electrodeposition processes, very minor amounts of impurities can have a major effect on the operation of the process and the quality of the product. In the electrowinning of zinc, for example, the current efficiency is sensitive to antimony in the parts per billion range since very small amounts of antimony apparently materially lower the hydrogen overvoltage, thus diverting a considerable portion of the electrolytic current to the liberation of hydrogen rather than the deposition of zinc. Relatively larger, but nonetheless very minor, amounts of more noble metals such as silver, gold, copper, platinum, cobalt and nickel also lower hydrogen overvoltage by plating out on the cathode. Antimony, together with germanium, selenium or tellurium, may have the further adverse effect of promoting the redissolution of zinc with a consequent catastrophic effect on current efficiency.

Although antimony is commonly present as an impurity in zinc electrowinning solutions and has a highly adverse effect on current efficiency, the presence of very small amounts of antimony has the favorable effect of inhibiting the nonreleasable sticking of zinc to the aluminum cathodes conventionally used in zinc electrowinning. Moreover, the catastrophic adverse effect on current efficiency caused by excess antimony can be largely offset by the presence of a protein glue additive. In a similar fashion, minor proportions of 1-nitroso-2-naphthol tie up and offset the otherwise adverse effects of nickel and cobalt. Very minor amounts of a protein glue also promote a favorable zinc deposit morphology and prevent dendrite growth which could otherwise lead to cell shorting.

In the electrodeposition of copper, relatively minor amounts of chloride ion normally have a polarizing effect, reducing current densities at given voltages. Other additives such as glue, thiourea and anionic flocculating agents may also have significant effects on deposit morphology and/or other important aspects of the electrodeposition process. Control of morphology is a major problem in copper electrodeposition processes.

Because of the strong influence of very minor proportions of impurities and additives, normal quantitative analytical techniques are not effective in predicting the performance characteristics of an electrolytic solution used in an electrodeposition process. For this reason, such techniques are often inadequate to provide definitive guidance for the treatment necessary to improve the performance of a solution already charged to the cells. Moreover, such analyses as can be made frequently do not directly or readily correlate with performance characteristics. Under current practice in zinc electrowinning, for example, additions of additives such as glue may be made in response to plant observations but the number of variables which affect the ultimate plant response, together with the significant impact of very minor proportions of glue, result in the process control procedure being a somewhat hit-and-miss, trial-and-error proposition.

Further problems may be encountered in electrodeposition processes because of imperfections in the electrodes. In zinc electrowinning, for example, the presence of an oxide coating on the aluminum cathodes is essential to prevent sticking of the deposited zinc to the cathodes. Prior to the present invention, however, there have been few, if any, highly reliable techniques for predicting the performance of a cathode before it is installed in a commercial cell.

If more definitive process measurement and control techniques were made available, significant improvements could be made in the economy and reliability of various electrodeposition processes. Thus, for example, if a technique were available by which the current efficiency obtainable from a particular electrolytic solution could be quickly and reliably predicted before that solution is delivered to the electrolytic cell, the average current efficiencies achieved could be materially increased. If a quantitative determination could be made of the minor amounts of impurities which significantly affect current efficiency, a further major advantage could be realized both with respect to control of the electrolytic solution delivered to the cells and with respect to the control of additives by which cell liquor composition can be modified. A still further major advantage would arise from the capability of preventing dendrite growth or other morphological defects rather than attempting to correct these tendencies once they have been observed in the cell.

SUMMARY OF THE INVENTION

Among the several objects of the present invention, therefore, may be noted the provision of improved methods for detecting impurities or additives in electrolytic solutions for the electrodeposition of metals; the provision of such methods which effectively predict the current efficiency obtainable from a given electrolytic solution or system; the provision of such methods which can be utilized to evaluate electrodes in the electrodeposition process; and the provision of improved methods of process control using such methods of measurement. Other objects and features will be in part apparent and in part pointed out hereinafter.

Briefly, therefore, the present invention is directed to a method of evaluating an unknown electrolytic system comprising an electrolytic solution and electrodes for the electrodeposition of metals with respect to determining the performance characteristics of the electrolytic solution, detection of impurities and additives in the electrolytic solution, estimation of the current efficiency characteristics of the system, or determining the performance characteristics of an electrode. In this method, an electrolytic circuit is established comprising a sample of the solution, two electrodes immersed in the solution and spaced from one another therein, and a variable and reversible voltage source having its output terminals respectively connected to the electrodes. A predetermined initial voltage is applied to one of the electrodes constituting a working electrode. This voltage is varied in the negative direction until a predetermined cathodic current or a predetermined maximum voltage sufficient to cause a cathodic reaction is attained at the working electrode. The direction of the change of voltage is thereafter reversed to vary the voltage in the positive direction until a predetermined minimum voltage or predetermined minimum current is attained at the working electrode. The negative voltage movement, reversal and positive voltage movement are repeated through a plurality of cycles, and the current obtained is recorded as a function of voltage for a selected cycle or cycles. From the recorded relationship between current and voltage, the performance characteristics of the sample solution, the presence of an impurity or additive, the current efficiency, or the working electrode characteristics are determined.

The invention is further directed to a process control method in which corrective action is taken based on evaluation of the electrolytic solution or electrodes by cyclic voltammetry.

DESCRIPTION OF THE PREFERRED EMBODIMENT

Figure 2:
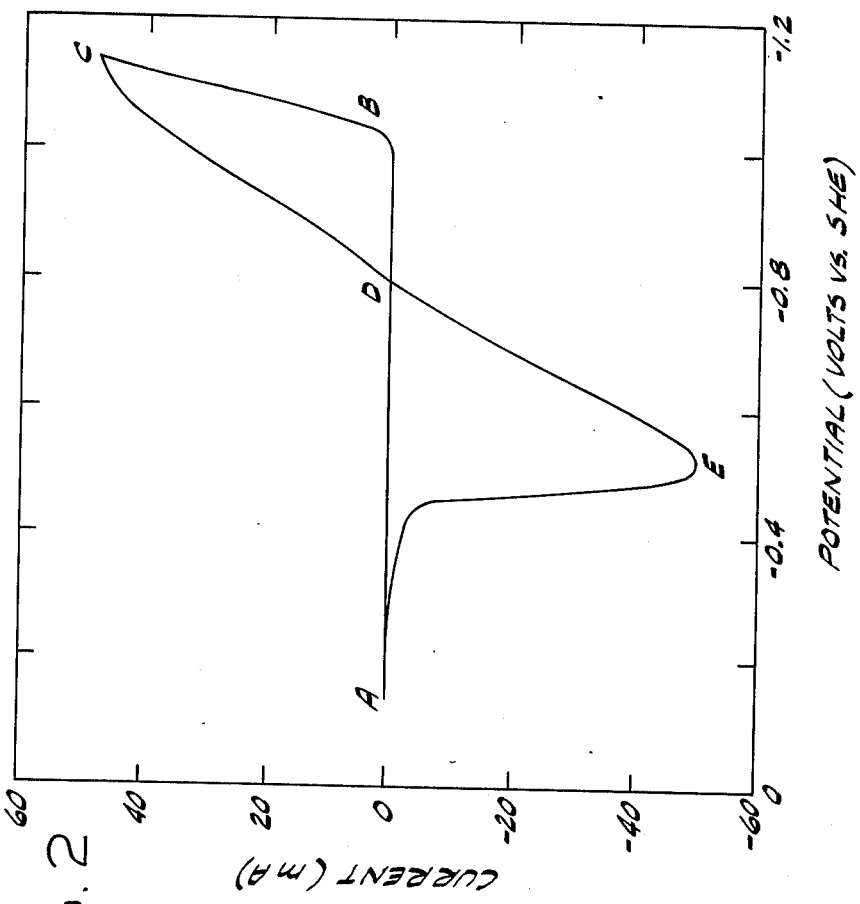
FIG. 2 is a cyclic voltammogram for acidified zinc sulfate electrolyte (0.77 molar $Zn^{++}$, 1 molar $H_2SO_4$)

In accordance with the method of the invention, a cyclic voltammogram is taken, utilizing any apparatus capable of driving a variable and measurable voltage through a cycle of sufficient extent to cause a measurable cathodic current at a working electrode when the voltage is driven in the negative direction. Preferably, the apparatus may also produce a measurable anodic current when the voltage is driven to the positive end of the range. A typically useful apparatus is that depicted in FIG. 1. In this apparatus the electrolytic solution is contained in a "Pyrex" H-cell 1, a working electrode 3 is immersed in the solution in one leg 5 of cell 1, and an auxiliary electrode 7 is immersed in the other leg 9. A reference electrode 11 is located in electrode chamber 13 in communication with leg 5. Potentiostat 15 is adapted to measure and control the voltage of electrode 3 with reference to electrode 11, and to detect and measure any current in the circuit comprising the voltage source within the potentiostat, the electrolytic solution, electrode 3 and electrode 7.

A voltage scan generator 17 drives potentiostat 15 in a voltage sweep extending alternately in the negative and positive directions. The voltage differential between working electrode 3 and reference electrode 11 is continuously measured by electrometer 19, the current in the electrolytic circuit is continuously measured by potentiostat 15, and both current and voltage measurements are continuously transmitted to X-Y recorder 21 where current is continuously plotted on a grid as a function of voltage.

In carrying out a cyclic voltammetric measurement, the electrolytic solution is delivered to H-cell 1 with electrodes 3 and 11 immersed therein. Preferably, the system constituted by the solution and electrodes 3 and 11 is maintained at open-circuit potential for a period sufficient to allow the system to come to chemical equilibrium. This period may range from a few minutes to several hours or more. Once the system is considered to be at chemical equilibrium, a predetermined initial voltage (referenced to electrode 11) is applied to electrode 3 by the voltage source within the potentiostat 15. By operation of voltage scan generator 17, the voltage is then continuously varied in the negative direction to a predetermined maximum voltage sufficient to cause a cathodic reaction at electrode 3. Once the predetermined maximum voltage has been reached, the voltage scan generator reverses the direction of voltage scan and moves the voltage continuously in the positive direction, until a minimum voltage is attained at electrode 3. Depending on the specific property to be determined, the reverse scan may extend to a voltage sufficiently positive to cause an anodic reaction at electrode 3. For purposes of this disclosure, maximum voltage means the most negative voltage attained and minimum voltage means the most positive voltage attained.

In order to obtain the most meaningful, reliable results and avoid damage to electrode 3, the initial voltage is preferably chosen at a level at which there is no anodic current, most preferably no initial current at al. Normally, the first cathodic scan proceeds directly from the initial voltage, but an anodic scan may precede the first cathodic scan, if desired, provided that no substantial initial anodic current is drawn. The maximum (most highly negative) voltage is arbitrary but is preferably high enough to achieve a current in the range in which the current response is approximately linear with voltage and in which errors in current measurement represent a minimal fraction of total current. The minimum (most positive) voltage on the reverse sweep may also be arbitrarily chosen, but to obtain measurements of current efficiency, it is important that the voltage be sufficiently positive to produce an anodic current, and that the anodic current be maintained for a sufficient period of time to insure essentially complete redissolution of metal deposited during the cathodic current phase of the cycle.

Figure 1:
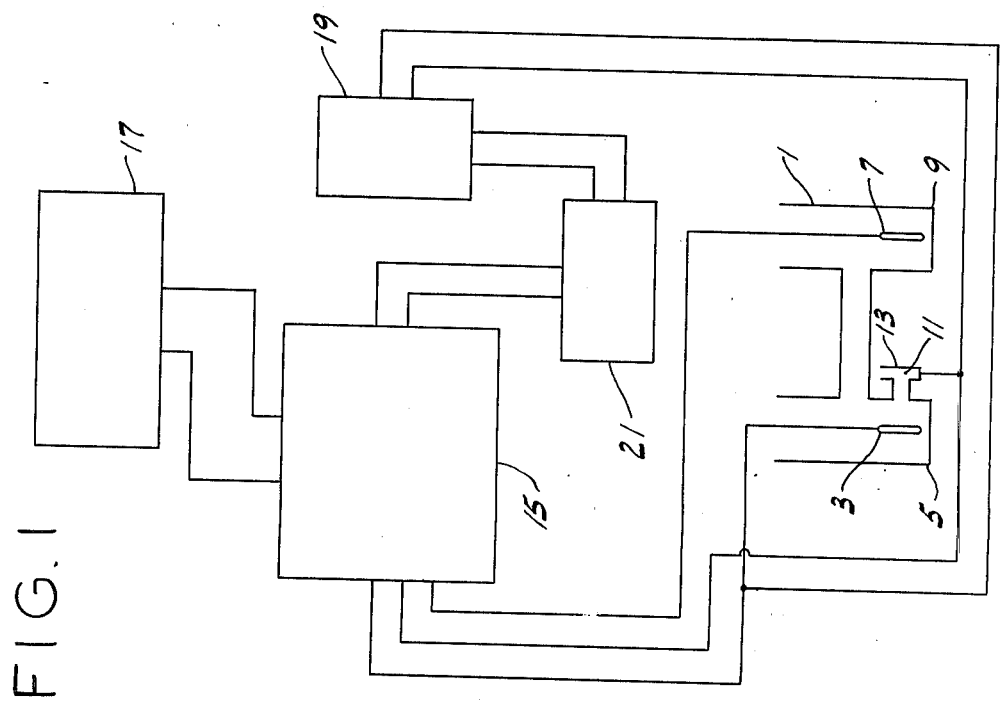
FIG. 1 is a schematic diagram indicating the apparatus utilized to obtain cyclic voltammograms in the method of the invention.

Although the apparatus shown in FIG. 1 is adapted for control of the voltage sweep cycle by maximum and minimum voltages, those skilled in the art will appreciate that instrumentation could be employed by which the negative (cathodic) sweep is terminated at a predetermined cathodic current and the positive (anodic) sweep is terminated at a predetermined minimum current. Minimum current is here defined as a lowest cathodic current or highest anodic current used as the termination point of the anodic sweep.

The voltage sweep rate is typically in the range of 1 to 100 mv/sec, although rates outside this range can be utilized. It is important that a predetermined and consistent rate or schedule of rates be utilized, particularly where an unknown electrolytic solution is being evaluated by a comparison with the curves obtained from known solutions in accordance with the method described more fully hereinbelow. Desirably, a relatively high sweep rate is utilized where the electrode reaction involved is diffusion controlled. Reproducibility is also enhanced where a relatively high sweep rate is used. In some determinations, a series of sweep rates may be used to take a series of voltammograms, since the differential between voltammograms obtained at different sweep rates may yield particularly useful information.

In order to obtain a voltammogram which is most highly indicative of the performance of an electrode and/or electrolytic solution under commercial process conditions, cyclic voltammetric measurements should be carried through a plurality of cycles sufficient to establish a pseudoequilibrium. At the pseudoequilibrium, the pen of the X-Y recorder retraces a substantially identical curve over a series of cycles. The initial transient cycles, however, may also yield useful information.

The temperature of the electrolytic solution should be maintained substantially constant while the voltammogram is being obtained. The control temperature is not normally critical. As in the case of sweep rate, the differential between cyclic voltammograms obtained at different temperatures may also yield useful information. Relatively drastic changes in the voltammogram may be observed with changing temperature where adverse concentrations of certain impurities are present.

FIG. 2 shows a typical cyclic voltammogram of the type developed in the course of carrying out the method of this invention. The voltage coordinate of point A is the starting potential, and the voltage coordinate of point B is termed the decomposition potential. The maximum voltage and cathodic current are reached at point C where the voltage sweep direction is reversed. From point C the sweep proceeds in an anodic direction to point D whose voltage coordinate is the crossover potential at which the net current flow is zero. The maximum anodic current is reached at point E, after which the current rapidly falls off to zero as the metal deposited during the cathodic current phase of the cycle is completely redissolved. In FIG. 2, the minimum voltage is reached at point A, and is thus essentially the same as the initial voltage but, as those skilled in the art will understand, these two voltages do not necessarily coincide.

Considering the voltage coordinate of A as the initial voltage, the curve ABC represents the cathodic current/cathodic sweep portion of the voltammograph, while the segment CD is the cathodic current/anodic sweep portion thereof. Curve DEA is the anodic current/anodic sweep portion.

Although the techniques of obtaining cyclic voltammograms are known and cyclic voltammetry has been utilized for purposes such as the study of organic and inorganic redox reaction mechanisms, I have discovered that cyclic voltammetry may be utilized in a novel and highly effective method of evaluating unknown electrolytic systems from the standpoint of determining the performance characteristics of the electrolytic solution, the detection of impurities or additives in the electrolytic solution, estimation of current efficiency characteristics of the solution or system, and determination of the performance characteristics of the electrodes. The method which I have thus devised provides a unique and practical process control tool which allows a commerical zinc electrowinning, copper electrowinning, copper electrorefining, or other metal electrodeposition process to be operated at higher current efficiencies and consequent lower cost. The method of the invention further affords the basis for improved control of metal deposit morphology, and in particular control of the growth of dendrites which may otherwise cause shorting in the electrolytic cell.

In utilizing the method of the invention to detect the presence and approximate concentration of impurities and/or additives in an unknown electrolytic solution, the composition of the solution is initially determined with regard to the principal electrolytes and other principal components by conventional analytical techniques. A cyclic voltammogram is taken of the unknown solution and compared with standard voltammograms taken on known solutions having the same composition of electrolyte and other principal components as the unkown solution, and varying proportions of common impurities, additives and combinations thereof. Both the unknown and standard voltammograms should be taken with the same terminal voltages (or currents) and sweep rates, at the same temperature, and using the same electrodes. Matching of the voltammogram for the unknown with a standard voltammogram of known composition provides a uniquely accurate and effective determination of the presence and concentration of the additive or impurity in the unknown solution.

In the case of zinc electrowinning solutions, for example, a common impurity is antimony and a common additive is protein glue. As noted above, antimony may also be employed in small quantities as an additive to promote release of electrodeposited zinc from an aluminum cathode. The presence of antimony tends to lower the hydrogen overvoltage and thus the decomposition voltage of the electrolytic solution. As a consequence, the line BC in FIG. 2 is typically moved to the left by a distance which is a function of the concentration of antimony in the electrolytic solution. Glue, on the other hand, tends to have a blocking effect on the deposition of zinc at the electrode, and thus creates a penetration overvoltage which increases the decomposition potential and moves the line BC to the right by a distance which is a function of the glue concentration. Because of the blocking effect of glue on the deposition of zinc, the current falls rapidly with decreasing voltage on the cathodic current/anodic sweep (CD) portion of the voltammogram and approaches the crossover potential D at a markedly reduced slope. The blocking effect of glue also appears to inhibit the redissolution of zinc during the anodic sweep/anodic current (DE) portion of the voltammogram, at least until a certain breakthrough voltage is reached. As a result, the shallow slope portion which initiates on the cathodic current side extends through the crossover potential to give a shallow sloped segment whose slope and terminal inflection points are characteristic of the concentration of glue in the zinc electrowinning solution.

It is known that combinations of impurities in electrolytic solutions often exhibit synergistic effects which may vary widely from the additive effect of the two or more impurities considered singly. This phenomenon has been observed, for example, in zinc electrowinning solutions containing both glue and antimony and presents a particularly serious obstacle to the effective evaluation of such solutions by simple chemical analysis. In accordance with the present invention, however, it has been discovered that the cyclic voltammogram characteristic of a solution containing both glue and antimony provides a very useful guide for predicting the solution's performance in an electrolytic cell. In effect, therefore, the impact of the syngerism can be effecitvely evaluated and an indication of any necessary corrective action obtained in a manner that chemical analysis alone cannot provide. Thus, for example, once the pseudo-equilibrium is reached after a number of cycles between the maximum and minimum voltage, a measurement of the decomposition potential is obtained which provides a useful guide to the hydrogen overvoltage and cell voltage to be anticipated if the electrolytic solution is utilized in a commercial operating cell. Moreover, the cathodic current/anodic backsweep (line CD in FIG. 2) provides an especially useful indication of how the electrolytic solution will behave where the metal from the solution is deposited on itself as in the operation of a commercial cell. Additionally, the approach to crossover is an indication of penetration overvoltage and a basis for projecting the effect of this phenomenon in cell operation.

A particularly advantageous aspect of the present invention is its capability of predicting the current efficiency obtainable from an electrolytic system. In making current efficiency determinations, the sweep rate must be kept constant, or at least recorded with respect to voltage. In the cathodic current portion of the sweep (ABCD), a cathode reaction occurs which typically includes both the deposition of metal and the liberation of hydrogen. Liberation of hydrogen, of course, is an unwanted result, and to the extent that this occurs current efficiency is reduced. In the anodic current portion of the curve (DEA), however, the only significant electrode reaction is the redissolution of metal. Provided that an anodic current is maintained for a period long enough to redissolve all of the metal deposited during the cathodic current phase of the voltammetric sweep, the electrical work done during the anodic current portion of the cycle, proportional to the area under the curve DEA when the sweep rate is constant, represents the energy required to carry out the electrode reaction with respect to the oxidation of the metal alone. Since the electrical work done during the cathodic current portion of the cycle, proportional to the area under the curves ABC and CD at constant sweep rate, constitutes the energy required to both deposit the metal and liberate hydrogen, the ratio of the area BEA to to ABCD provides an indication of the cathodic energy required to deposit the metal versus that required to reduce hydrogen ions. Thus, this ratio is a direct function of the current efficiency. In this connection, it may be noted that the presence of impurities in the electrolytic solution does not have any material effect on the crossover potential (i.e., the voltage coordinate of point D). Thus the impurities' presence and effect as indicated by the method of the invention do not affect the thermodynamics of the electrolytic reactions involved, but have effects on the kinetics which are indicated by the shapes of the voltammograms obtained.

Although the ratio of anode to cathode current energies may be mathematically translated into current efficiencies, a more convenient translation may be made by comparing the ratio obtained with the ratios obtained from known systems having similar electrodes and solution compositions and known current efficiencies. Because current efficiencies typically vary with current density, it is essential that the unknown and standard voltammograms be taken with the same maximum current densities as well as the same temperature. The sweep rate schedule should also be at least approximately the same.

Further, in accordance with the invention, cyclic voltammograms can be used to evaluate anodes and anode materials. Using a standard electrolytic solution and specified terminal voltages (or current), sweep rate schedule, and solution temperature, a library of cyclic voltammograms can be obtained for various types of electrodes and/or electrodes having various known defects. The performance of an unknown electrode may thereafter be predicted by obtaining its cyclic voltammogram in the same electrolytic solution and under the same conditions as the standard electrodes and then comparing the voltammogram obtained with those in the library.

The method of the invention may be utilized as a process control tool in a variety of ways. Thus both the initial charge to a commercial cell and makeup solution destined for that cell can be evaluated by cyclic voltammetry in a test circuit before delivery to the cell. If the electrode does not perform properly in the voltammetric test, it may be rejected and the adverse effect it would produce in the cell avoided. Similarly, solutions prepared for delivery to the cell may either be rejected or adjusted in composition in response to the detected effect of an impurity in a manner calculated to improve performance. After such adjustment, the altered solution can again be evaluated voltammetrically and this alternate procedure repeated until the solution provides a voltammogram characteristic of a solution affording good performance.

The method of the invention may also be utilized for process control by taking the cyclic voltammograms of samples of electrolytic solutions drawn from operating cells. Comparison of such voltammograms with standards provides an indication of how far the cell liquor may have strayed from optimum characteristics. Such comparison further provides an indication of what type of compositional adjustment may be needed to improve cell performance. A particularly advantageous feature of the method of the invention is the opportunity to make initial adjustments to the sample solution and redetermine its voltammogram and associated performance before risking adjustment of the cell liquor itself. Repeated adjustments and retesting of samples taken from the cells can lead to an optimum prescription for cell liquor composition adjustment before any action is taken in the plant.

The following examples illustrate the invention.

EXAMPLE 1

Cyclic voltammetry experiments were conducted on zinc sulfate electrowinning solutions utilizing apparatus of the type depicted in FIG. 1. In these experiments a carbon rod counter electrode was utilized and reference electrode 11 was a 1 molar mercurous sulfate electrode with an emf of 0.64 v versus a standard hydrogen electrode (SHE). Working electrode 3 was a 1.22 cm diameter rod of aluminum pressed into an embedded in a "Teflon" holder with its end face exposed to the electrolytic solution. The exposed area of the aluminum cathode was 1.18 cm$^2$ and the rod analyzed at 99.99+% aluminum, 0.002% silicon, 0.003% iron, and 0.003% copper. Before each voltammogram was taken, the cathode was prepared by polishing it with 600-grit Carbimet paper, the final pass being made on an unused portion of the paper. The polished surface was then cleaned by patting with an acetone-soaked tissue and finally raised with distilled water.

Voltage scan generator 17 was a Wenking model VSG-72, while potentiostat 15 was a Wenking potentiostat model 70-HP-10. X-Y recorder 21 was a Moseley 135AM.

An electrolytic solution was prepared by mixing neutral purified zinc sulfate solution having a pH of 5 (327 ml) taken from a commercial sulfide leach circuit, concentrated sulfuric acid (55 ml), and distilled water (618 ml). The solution obtained was approximately 1 molar $H_2SO_4$ and 0.77 molar zinc. Cyclic voltammograms were taken on this solution both in the pure state and with additions of antimony, glue, silver, copper, and nickel additives.

When the effects of antimony and glue were studied, the additives were initially mixed with the electrolytic solution in a beaker, and the mixture was thereafter introduced into the H-cell. Premixing overcame possible concentration gradients which might have resulted if the impurities were pipetted directly into the H-cell. The aluminum cathode was immersed in the electrolytic solution for thirty minutes before the cycle was begun, and prepurified nitrogen was bubbled continuously in both compartments of the H-cell during the entire run. Where copper, silver, and nickel additives were studied, the cathode was held in contact with the electrolytic solution at open-circuit potential for longer periods of time (i.e., twelve to forty-eight hours).

Various sweep rates were utilized with 1 mv/sec providing the most consistent results. In taking these voltammograms, the cycle was set to begin at an initial voltage of −0.46 v versus the standard hydrogen electrode with the maximum voltage set at a value capable of producing a total current of about 50 ma. At this point, the voltage sweep was reversed and the voltage driven anodically to the original starting potential. The temperature of the solution was maintained at 25° C. for each voltammogram.

In the voltammetric analyses prepared for glue and antimony additions, the following proportions were utilized:

| Run Number | Concentration |
|---|---|
| 1 | No addition |
| 2 | 10 ppm glue |
| 3 | 20 ppm glue |
| 4 | 40 ppm glue |
| 5 | 10 ppb antimony |
| 6 | 20 ppb antimony |
| 7 | 40 ppb antimony |
| 8 | 20 ppb antimony and 10 ppm glue |
| 9 | 40 ppb antimony and 10 ppm glue |
| 10 | 40 ppb antimony and 20 ppm glue |
| 11 | 40 ppb antimony and 40 ppm glue |
| 12 | 40 ppb antimony and 80 ppm glue |

Figure 3:
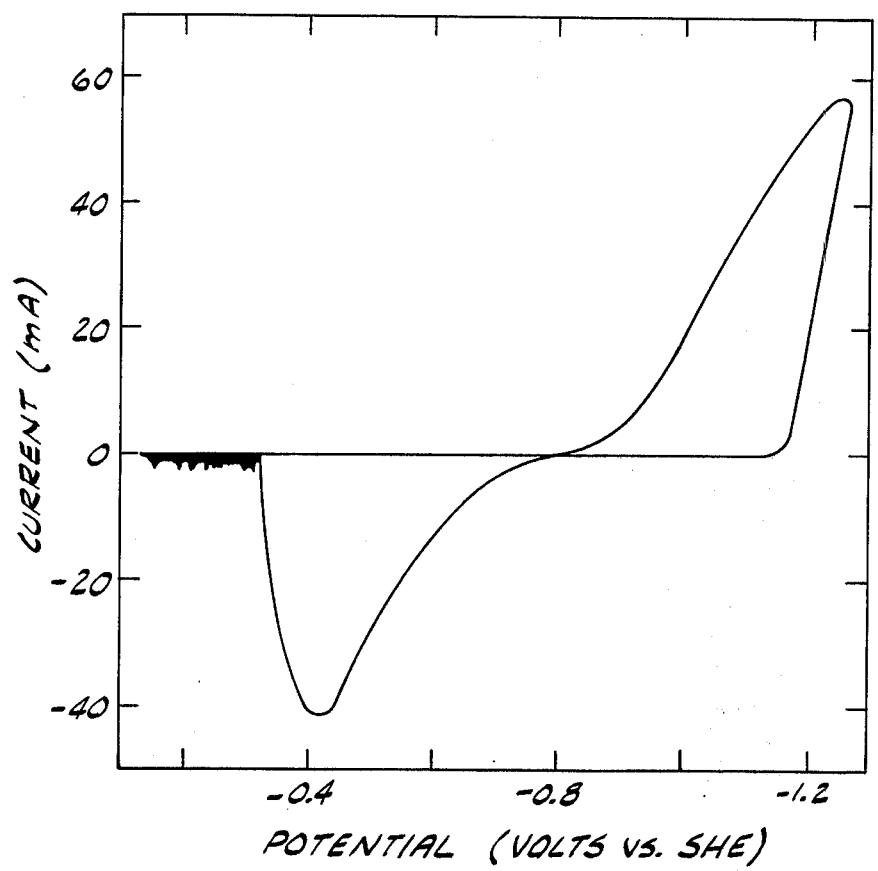
FIG. 3 is a cyclic voltammogram for acidified zinc sulfate electrolyte (0.77 molar $Zn^{++}$, 1 molar $H_2SO_4$) containing 40 ppm glue.
Figure 4:
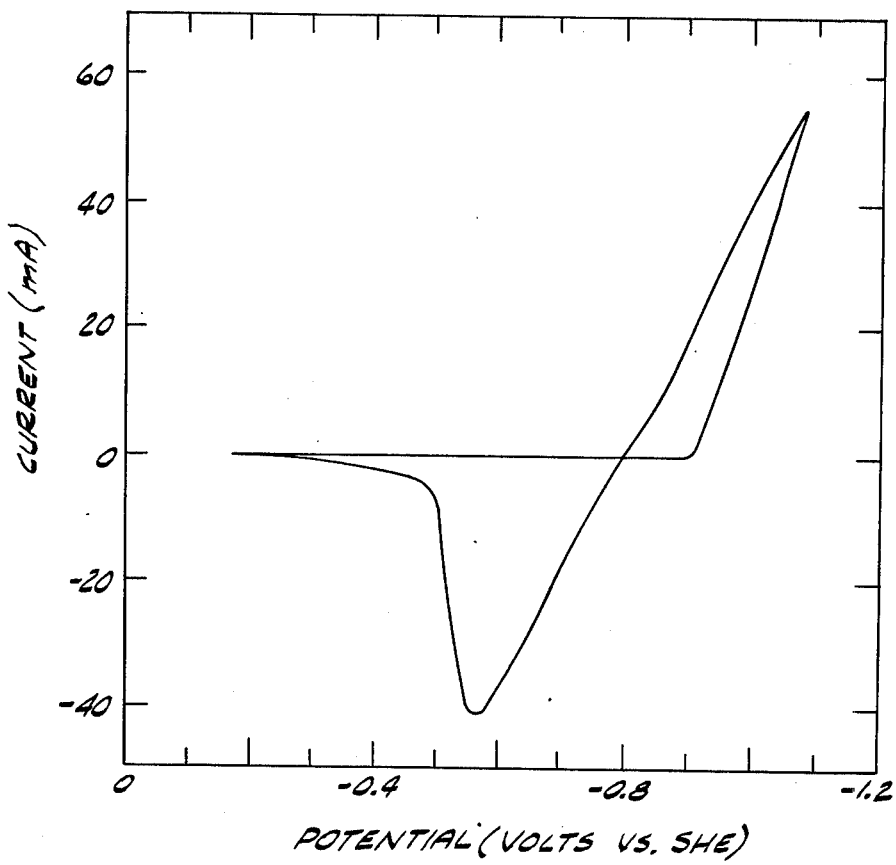
FIG. 4 is a cyclic voltammogram for acidified zinc sulfate electrolyte (0.77 molar $Zn^{++}$, 1 molar $H_2SO_4$) containing 40 ppb antimony.
Figure 5:
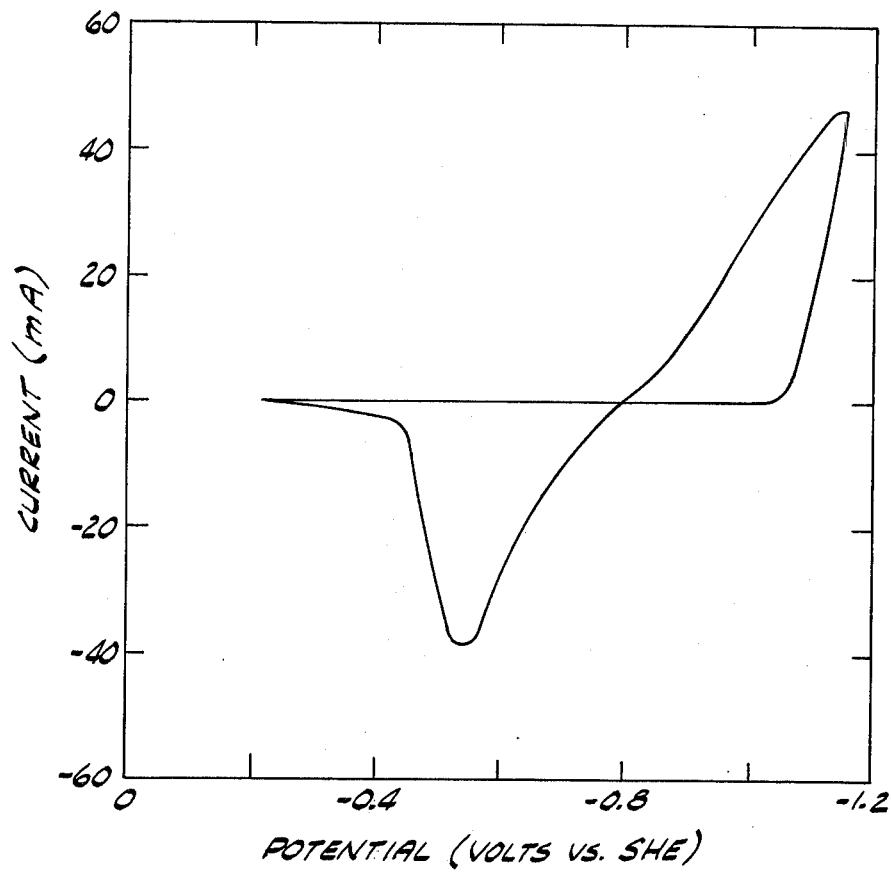
FIG. 5 is a cyclic voltammogram for acidified zinc sulfate electrolytic solution (0.77 molar $Zn^{++}$, 1 molar $H_2SO_4$) containing 40 ppb antimony and 20 ppm glue.

Set forth in Table 1 are the current levels attained at specified potential intervals past crossover at pseudo-equilibrium in the cyclic voltammograms of the acidified $ZnSO_4$ solutions containing glue and/or antimony. These current levels give a relative measure of the extent of polarization of the electrolytic solutions utilized in the study of antimony and glue additions. Typical voltammograms for 40 ppm glue, 40 ppb Sb and 40 ppb Sb-20ppm glue are shown in FIGS. 3, 4, and 5, respectively.

TABLE 1

CURRENT (MA) PRODUCED AT SPECIFIC POTENTIAL INTERVALS PAST CROSSOVER FOR 0.77 M $Zn^{++}$, 1 M $H_2SO_4$ SOLUTIONS

| Run | Concentration | mv Past Crossover (ABC Portion of Curve) | | | | | | |
|---|---|---|---|---|---|---|---|---|
| | | 50 | 75 | 100 | 125 | 150 | 175 | 200 |
| 1 | No additions | 0 | 0 | 0.25 | 8.0 | 28.0 | 50.0 | — |
| 2 | 10 ppm glue | 0 | 0 | 0 | 0 | 0.5 | 9.0 | 33.0 |
| 3 | 20 ppm glue | 0 | 0 | 0 | 0 | 0.25 | 2.5 | 21.0 |
| 4 | 40 ppm glue | 0 | 0 | 0 | 0 | 0 | 0.75 | 15.0 |
| 5 | 10 ppb Sb | 0 | 3.0 | 12.5 | 26.0 | 42.0 | — | — |
| 6 | 20 ppb Sb | 0 | 5.5 | 16.0 | 27.0 | 42.0 | — | — |
| 7 | 40 ppb Sb | 0.5 | 12.0 | 25.0 | 41.0 | 58.0 | — | — |
| 8 | 20 ppb Sb - 10 ppm glue | 0 | 0 | 0 | 3.0 | 20.0 | 43.0 | 64.0 |
| 9 | 40 ppb Sb - 10 ppm glue | 0 | 0 | 0 | 5.0 | 22.0 | 47.0 | 68.0 |
| 10 | 40 ppb Sb - 20 ppm glue | 0 | 0 | 0 | 2.0 | 20.0 | 46.0 | 66.0 |
| 11 | 40 ppb Sb - 40 ppm glue | 0 | 0 | 0 | 0 | 1.0 | 19.0 | 46.0 |
| 12 | 40 ppb Sb - 80 ppm glue | 0 | 0 | 0 | 0 | 0 | 2.0 | 18.0 |

| Run | Concentration | mv Past Crossover (CD Portion of Curve) | | | | | | |
|---|---|---|---|---|---|---|---|---|
| | | 10 | 20 | 30 | 40 | 50 | 60 | 70 |
| 1 | No additions | 2.50 | 5.25 | 8.00 | 11.50 | 15.00 | 17.00 | 19.00 |
| 2 | 10 ppm glue | 1.00 | 2.00 | 3.50 | 5.25 | 7.50 | 10.00 | 13.00 |
| 3 | 20 ppm glue | 0.75 | 1.50 | 2.50 | 3.50 | 6.0 | 8.50 | 11.00 |
| 4 | 40 ppm glue | 0.50 | 1.00 | 1.50 | 2.50 | 3.50 | 5.00 | 7.50 |
| 5 | 10 ppb Sb | 2.50 | 5.50 | 9.00 | 13.00 | 17.50 | 21.50 | 25.00 |
| 6 | 20 ppb Sb | 2.00 | 4.50 | 7.50 | 11.00 | 15.00 | 19.00 | 23.00 |
| 7 | 40 ppb Sb | 2.50 | 5.50 | 9.00 | 13.00 | 17.00 | 21.00 | 26.00 |
| 8 | 20 ppb Sb - 10 ppm glue | 1.00 | 3.00 | 5.00 | 8.00 | 11.00 | 13.00 | 15.00 |
| 9 | 40 ppb Sb - 10 ppm glue | 1.00 | 3.50 | 6.50 | 9.50 | 13.00 | 18.00 | 22.00 |
| 10 | 40 ppb Sb - 20 ppm glue | 1.00 | 2.00 | 3.00 | 4.50 | 7.00 | 10.00 | 13.00 |
| 11 | 40 ppb Sb - 40 ppm glue | 0.50 | 1.25 | 2.00 | 3.25 | 4.50 | 6.50 | 9.00 |
| 12 | 40 ppb Sb - 80 ppm glue | 0.50 | 1.25 | 1.75 | 2.25 | 3.00 | 4.00 | 5.00 |

The data of Table 1 show increased polarization and higher values of decomposition potential, the degree of which was proportional to the concentration of glue added. This is graphically illustrated in FIG. 6 which shows the cathodic current/cathodic sweep (ABC) portion of the voltammogram for eight of the runs of Table 1. As this figure indicates, readily detectable changes in overpotential are produced by variations of 5-10 ppm in glue concentration. Thus cathodic potentials of 50, 62 and 74 mv at 10 ma cathodic current were obtained on the cathodic sweep with glue additions of 10, 20 and 40 ppm, respectively. The average increase in overpotential occurring between the 10 ppm and 20 ppm glue was nearly identical to that observed between 20 ppm and 40 ppm glue on the cathodic sweep. Thus a doubling of glue concentration in the range considered produced an average potential increase of about 12 mv. Even though the cathodic curves were shifted with increasing glue addition, the relative slope remained constant during the cathodic sweep.

Figure 7:
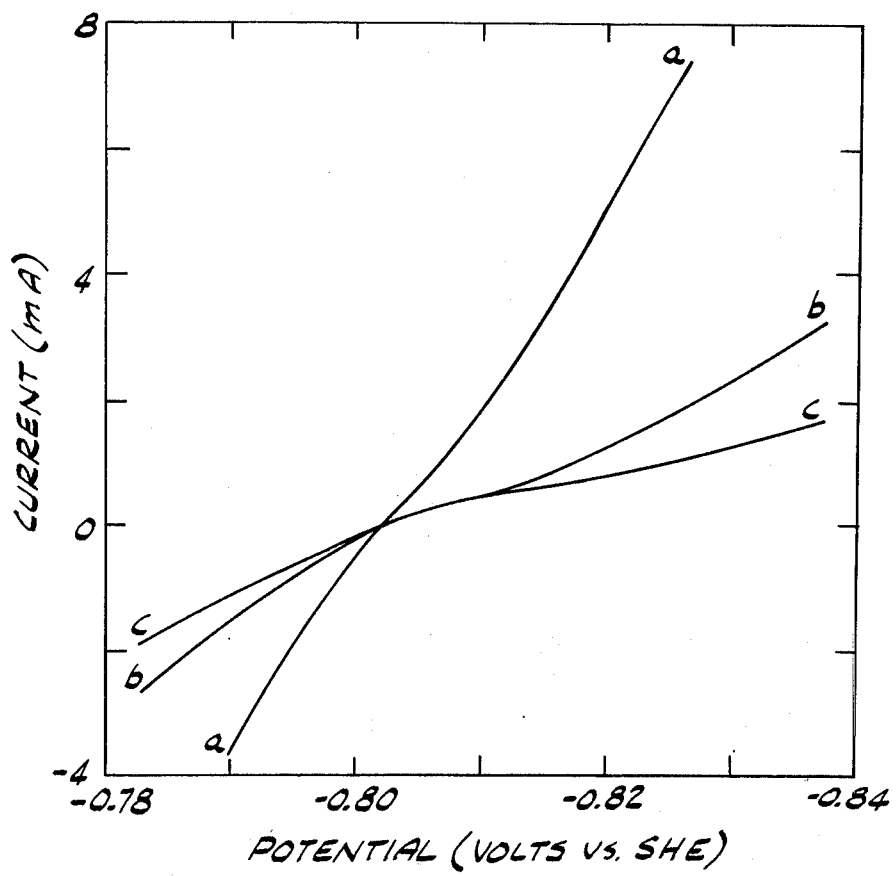
FIG. 7 shows a series of backsweep (anodic sweep) curves taken from the cyclic voltammograms for acidified zinc sulfate electrolytic solutions containing varying amounts of antimony and glue.

Another distinct characteristic of the voltammograms for zinc sulfate solutions containing glue was the shallow slope through the crossover point D. An expanded-scale view of this result is shown in FIG. 7. Where a glue additive is present, the slope through the crossover point was found to be an inverse function of glue content. It was observed that upon completion of the cycle, zinc flakes floated off the aluminum cathode, indicating incomplete anodic stripping. This accounts for the erratic current fluctuation indicated by the black area of the curve in FIG. 3 which was apparently caused by the flakes intermittently resuming contact with the aluminum or by general variations in the overall surface area of the zinc.

Figure 6:
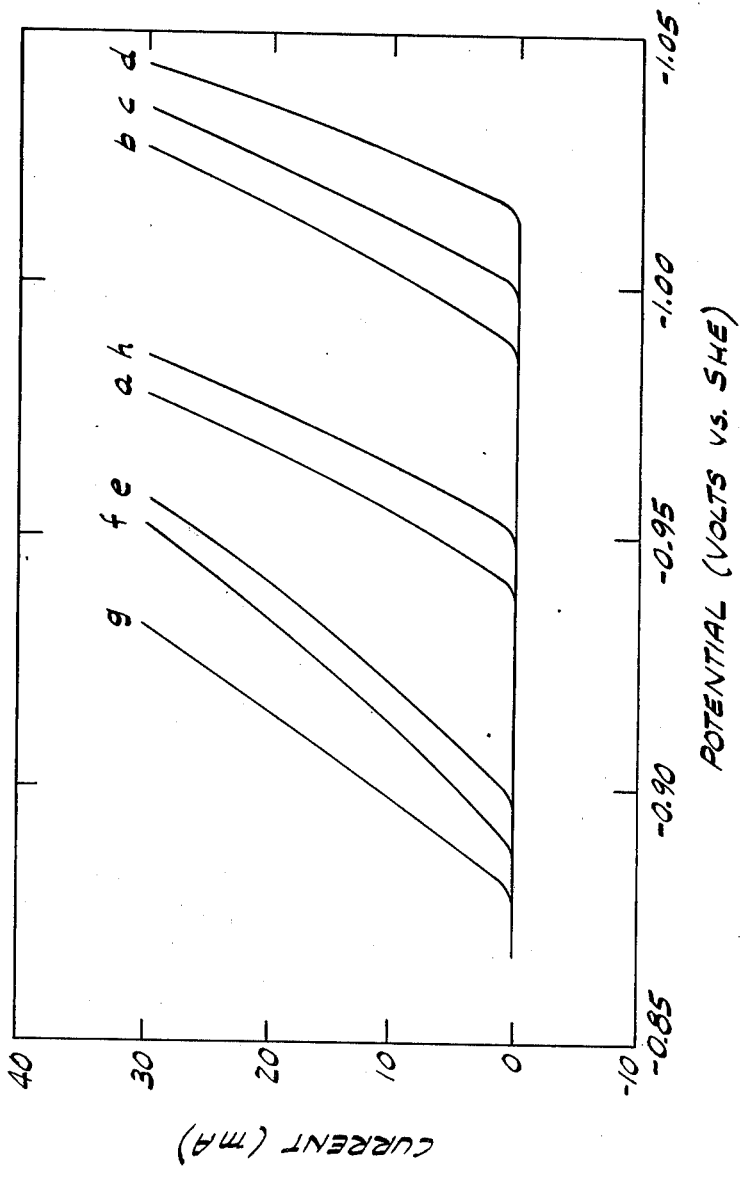
FIG. 6 shows a series of polarization curves for the cathodic current/cathodic sweep portion of the cyclic voltammograms for acidified zinc sulfate electrolytic solution (0.77 molar $Zn^{++}$, 1 molar $H_2SO_4$) containing various proportions of glue and/or antimony.

As indicted in FIG. 6, antimony addition resulted in marked depolarization, an effect opposite to that resulting from glue additions. In accordance with the method of this invention, changes in concentration as low as 5-10 ppb antimony can be detected by overvoltage differences as illustrated in FIG. 6. The decrease in overpotential was directly proportional to the concentration of antimony. A 43 mv decrease in the composition potential occurs for those solutions containing 10 ppb antimony as compared to pure zinc electrolytes. In contrast to the voltammograms obtained from zinc sulfate solutions containing glue, the slope through the crossover point was substantially linear and free of inflection points in the antimony voltammograms.

The cyclic voltammograms of FIGS. 3 and 4 confirm the industrial experience that antimony and glue additions produce opposite effects on the polarization curve. The interactions between glue and antimony were reflected in the voltammograms of electrolytic solutions containing combinations of 40 ppb antimony with 10, 20, 40 and 80 ppm glue, and 20 ppb antimony with 10 ppm glue. A representative voltammogram for 40 ppb antimony and 20 ppm glue is shown in FIG. 5. 40 ppb antimony with 40 and 80 ppm glue showed excess glue characteristics, as indicated by increased polarization for the cathodic sweep/cathodic current portion of the diagram and the shallow slope of the curve through the crossover potential. For 40 ppb antimony with 10 ppm glue and 40 ppb antimony with 20 ppm glue, only a slight excess glue effect was shown, but the combination of 40 ppb antimony with 10 ppm glue gave about the same characteristics as the pure electrolytic solution. Similar ratios, 40-80 ppb antimony to 15-30 ppm glue, were obtained in another study in which cathodic efficiencies were obtained for various glue and antimony additions. It was noted that for mixed additions, even with the proper ratio of additions to produce a cathodic polarization curve resembling that of the pure solution, the slope of the voltammogram is lower as it proceeds through crossover, and the anodic current portion is skewed in a manner similar to that for glue additions.

As an indication of current efficiency, the ratio of anodic to cathodic areas was determined for each of the runs of the example. The results of these computations are set forth in Table 2.

TABLE 2

RELATIVE ZINC DEPOSITION EFFICIENCIES FOR 0.77 M $Zn^{++}$, 1 M $H_2SO_4$ SOLUTIONS

| Run | Concentration | a/c Ratio |
| --- | --- | --- |
| 1 | No addition | 0.83 |
| 2 | 10 ppm glue | 0.62 |
| 3 | 20 ppm glue | 0.58 |
| 4 | 40 ppm glue | 0.58 |
| 5 | 10 ppb Sb | 0.73 |
| 6 | 20 ppb Sb | 0.57 |
| 7 | 40 ppb Sb | 0.61 |
| 8 | 20 ppb Sb 10 ppm glue | 0.75 |
| 9 | 40 ppb Sb 10 ppm glue | 0.78 |
| 10 | 40 ppb Sb 20 ppm glue | 0.76 |
| 11 | 40 ppb Sb 40 ppm glue | 0.72 |
| 12 | 40 ppb Sb 80 ppm glue | 0.52 |

The ratios of anodic to cathodic areas for glue additions ranged between 0.58 to 0.62 as compared to 0.83 for a pure acid zinc sulfate electrolytic solution, indicating a rather substantial decrease in efficiency. Although a part of this indicated inefficiency was due to incomplete anodic stripping, as previously mentioned, the amount of hydrogen which could be directly observed evolving from the cathode also seemed to be directly proportional to the quantity of glue in the solution.

The ratios of anodic to cathodic areas for antimony additions were 0.73, 0.57 and 0.61 for 10, 20 and 40 ppb antimony additions, respectively, indicating a probable decrease in current efficiencies with increasing antimony. With 40 ppb antimony present, a noticeable amount of hydrogen could be observed evolving from the aluminum surface as completion of the cycle was approached.

In the runs on solutions containing glue and antimony mixtures, the ratio of anodic to cathodic areas averaged about 0.75 which is intermediate between those for pure electrolytic solutions and single impurity additions.

EXAMPLE 2

Figure 8:
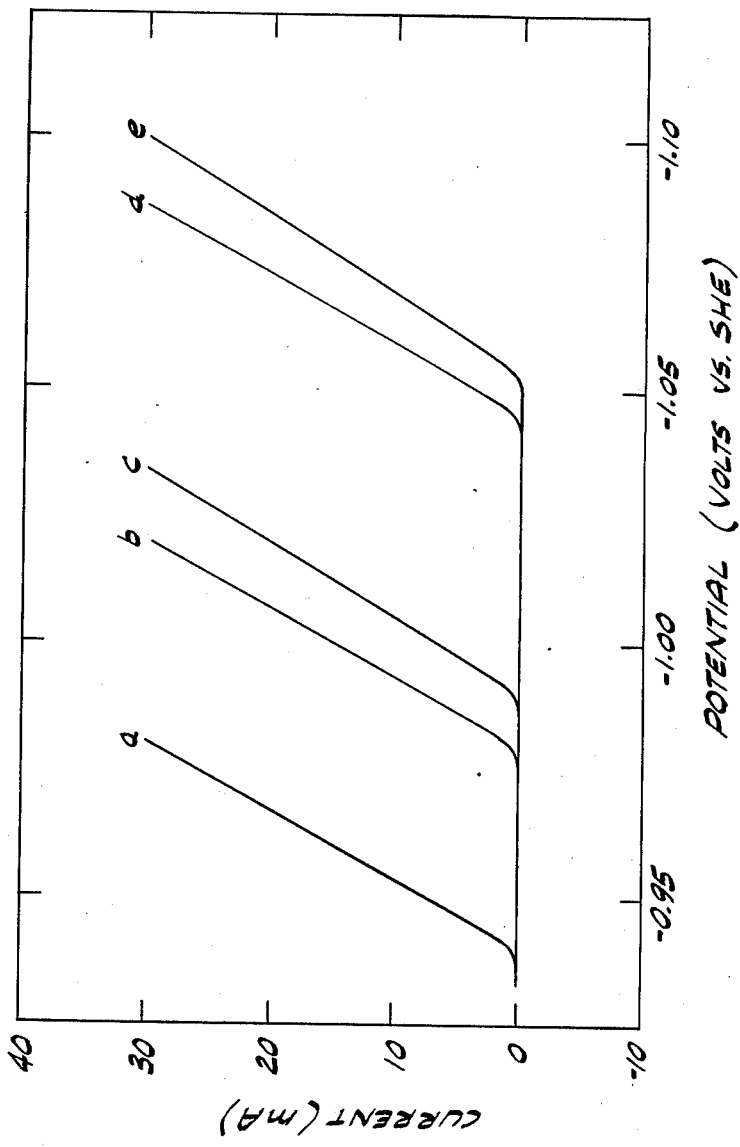
FIG. 8 illustrates the effect of sweep rate on the cathodic polarization curve for acidified zinc sulfate electrolytic solutions.

Utilizing the apparatus and the pure acidified zinc sulfate electrolytic solution described in Example 1, cyclic voltammograms were taken at varying sweep rates in order to determine the effect of this factor on the character of the voltammogram obtained. As indicated in FIG. 8 and Table 3, an inverse relationship between current efficiency and sweep rate was noted throughout the range investigated.

Where consecutive cycling was carried out at 1 mv/sec, the decomposition potential decreased with each succeeding cycle until the curves began to be reproducible after five to six cycles. After about six cycles, pseudoequilibrium was attained and the pen on the X-Y recorder traced over the same curve for successive cycles. The initial variation was most marked between the first and second cycles, and the rate of change decreased with each cycle. This effect is believed to be attributable to incomplete stripping of zinc during the anodic sweep, since small zinc particles were detected on the aluminum surface by scanning electron microscope examination after one complete cycle.

TABLE 3

| Sweep Rate | a/c Ratio |
| --- | --- |
| 1 mv/sec | 0.83 |
| 5 mv/sec | 0.71 |
| 10 mv/sec | 0.68 |
| 50 mv/sec | 0.48 |
| 100 mv/sec | 0.46 |

EXAMPLE 3

Deposit morphologies were determined for the electrolysis of acidified zinc sulfate solutions of the type described in Example 1. Where a pure solution was used, the zinc was observed to deposit evenly on the cathode with an average particle size of about 5 microns. Each crystal appeared to be growing independently of its neighbors with no tendency for the particles to join together. It was also evident that there was a substantial portion of the aluminum substrate which remained clear of zinc, indicating a limited amount of initial nucleation.

Deposits from antimony-containing solutions showed a marked increase in facet size (10 microns for 40 ppb antimony) and examination indicated that these deposits had a slight (0002) preferred orientation. The facet and crystallite size was directly related to antimony concentration.

Glue addition deposits showed an average facet size of one micron with a distinct orientation characteristic (1120) and the individual crystals (about 8 microns) tended to agglomerate more than those for deposits from pure electrolytic solution or solutions containing antimony. Each agglomerated island obtained from solutions containing glue appeared to run parallel to the striations on the anode surface which were produced in the polishing of the anode. A slight glue excess morphology existed for deposits containing 40 ppb antimony and 20 ppm glue additions. There appeared to be a substantial glue-like preferred orientation but the islands were more uniformly distributed over the aluminum cathode.

The results of the runs of this example illustrate that the method of the invention can be used as an effective process control tool in controlling deposit morphology. The known correlations which can be developed between morphology and additive or impurity content, together with the known correlations which can be established between impurity content and cyclic voltammograms, allow voltammograms to be used in determinig the adjustments to be made to provide the morphology desired.

EXAMPLE 4

Figure 9:
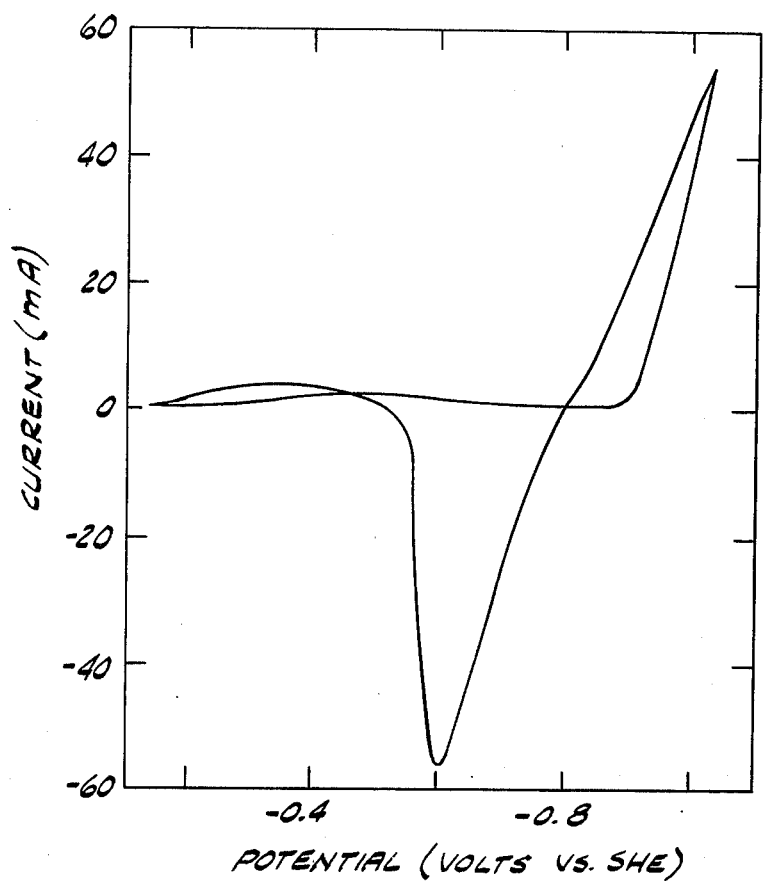
FIG. 9 is a cyclic voltammogram for acidified zinc sulfate electrolytic solution (0.77 molar $Zn^{++}$, 1 molar $H_2SO_4$) containing 2 ppm copper.

Utilizing the apparatus described in Example 1, cyclic voltammograms were taken for acidified zinc sulfate solutions containing additions of copper, silver and nickel. A representative voltammogram for copper additions is shown in FIG. 9. Distinguishable features of this voltammogram include the slight cathodic peak prior to the normal decomposition potential and also the substantial cathodic current generated on the anodic sweep after all the zinc had been redissolved. This peak was most probably produced by hydrogen, since large amounts of gas could be observed evolving from the cathode. The magnitudes of these two peaks were found to be directly proportional to the concentration of impurity and the length of time the cathode was held in contact with the electrolyte. Nondispersive X-ray analysis and scanning electron microscopy indicated that the copper and silver had plated onto the aluminum substrate, thus providing portions of the electrode surface at which the hydrogen overvoltage was significantly lowered.

EXAMPLE 5

Cyclic voltammograms were obtained on acidified copper sulfate solutions using an apparatus generally similar to that described in Example 1. However, in place of the aluminum cathode utilized in the voltammetric runs of Example 1, the cathode utilized in the runs of this example was copper prepared from high purity rod stock having a face surface area of 1.26 cm$^2$. The cathode was prepared for each experimental run by wet grinding using 240 to 600-grit Carbimet paper. The electrode was then washed with acetone in an ultrasonic cleaner, rinsed with acetone and dried in an air stream, and immediately placed in the H-cell.

The electrolytic solution utilized in the runs of this example was prepared from Fisher A300C sulfuric acid and copper sulfate pentahydrate. These two components were mixed with distilled water to obtain a concentration of 45 gpl $Cu^{++}$ and 200 gpl $H_2SO_4$. The copper concentration was determined by iodine-thiosulfate-starch titration, while the acid concentration was determined by titration with Fisher 1N sodium hydroxide standard solution. Before each experimental run the electrolyte concentration was checked and adjusted, as needed.

Cyclic voltammograms were obtained both for the unadulterated acidified copper sulfate electrolytic solution and for solutions containing additions of chloride ion, glue, flocculating agent (as sold under the trade designation "Separan" by the Dow Chemical Company) and thiourea, respectively. In each run a 300 ml aliquot of the electrolytic solution containing the appropriate proportion of additive was charged to the H-cell after which electrode 7 was placed in leg 9, reference electrode 11 installed in chamber 13, working electrode 3 inserted in leg 5, and a flow of prepurified nitrogen begun. Nitrogen flow was maintained throughout each run. Before application of a voltage from potentiostat 15, the cell was allowed to equilibrate for 15 minutes. In taking the voltammograms, voltage was initially applied at rest potential, approximately +0.285 v versus the standard hydrogen electrode. In each cycle for unadulterated solutions and those containing glue, chloride ion or "Separan", the voltage was increased in the negative direction to a maximum of −200 mv and then reversed and swept in the positive direction to a minimum voltage of zero volts. For solutions containing thiourea, the maximum voltage was −300 mv. In all cases, the scan rate was 1.0 mv/sec.

In certain of the runs of this example, copper electrodeposits were produced for examination by scanning electron microscopy. In these instances, attempts were made to produce copper deposits from different solutions on an approximately equal current basis. Thus the scan generator was engaged and the voltage scanned cathodically to a current density of 40 ma/cm$^2$, and then reversed and scanned in an anodic direction to a cathodic current of 16 ma/cm$^2$. To obtain these current densities, the working electrode was cycled to whatever minimum and maximum voltages were necessary to achieve these current densities and the electrode was held at the minimum voltage long enough to maintain a 16 ma/cm$^2$ current density for 60 sec. Thereafter, the electrode was immediately removed from the cell, washed with distilled water, rinsed with acetone, and dried in an air stream. This entire procedure was performed as rapidly as possible to prevent oxidation of the copper electrodeposit before it could be examined.

Voltammograms were obtained on the unadulterated acidified copper sulfate electrolytic solution at temperatures of 30°, 40°, 50° and 60° C. In obtaining these voltammograms, the voltage was cycled forward (cathodically) from rest potential to −200 mv overpotential and then back (anodically) to the original rest potential. In each of the curves obtained, the current generated during the anodic and cathodic sweeps was very similar. On the cathodic sweep, current initially increased at a high rate with respect to voltage and then tended to plateau out. The unadulterated electrolytic solution scan curves, which reflected progressive depolarization with increasing temperature, were used as a basis for comparison for the voltammograms obtained from electrolytic solutions with various additive agents.

Voltammograms were obtained using a copper cathode and acidified copper sulfate electrolytic solutions containing various proportions of chloride ion additive (HCl), glue, flocculating agent sold under the trade designation "Separan" by Dow Chemical Company, and thiourea. In taking these voltammograms, the voltage was cycled between a cathodic maximum overpotential of −200 mv and rest potential.

Voltammograms obtained from the solutions containing chloride ion were somewhat more polarized than those for unadulterated solutions but, as in the case of the unadulterated solutions, the relationship between current and voltage during the anodic sweep was very similar to that during the cathodic sweep. As in the case of the unadulterated copper sulfate solutions, increase of the electrolytic solution temperature at constant chloride ion concentration depolarized the deposition process, but at a given temperature, the effect of chloride ion was to cause polarization. The inhibiting effect of the chloride additive was apparently attributable to the formation of a copper chloride film on the cathode. The close similarity between the cathodic and anodic sweep curves indicates that this film remained stable or continued to form and affect the polarization behavoir at overpotentials up to −200 mv or more.

The copper cathode voltammograms obtained on electrolytic solutions containing glue or "Separan" additions resembled the voltammograms of the unadulterated solution except that the initial current plateau was shifted to a more cathodic position. The anodic sweeps were also always more polarized than the cathodic sweeps. Under isothermal conditions, increases in additive content increased the extent of polarization. Increasing the electrolytic solution temperature at constant additive concentration resulted in an increase in the magnitude of the plateau current, a shift of the initiation of the current plateau to more anodic overpotentials and a decrease in the breadth of the current plateau. Generally, the anodic sweeps were more reproducible since there was less influence from the original copper substrate and any oxide films or impurities initially present on its surface. The polarization observed when glue or "Separan" were present in the solution was attributable to the typical actions ascribed to organic additives, namely, adsorption film formation and inhibition. Both the cathodic and anodic sweep curves were substantially free of marked inflection points, thus indicating that no major change in the metal deposition mode cocurred over the overpotential range studied.

The copper cathode voltammograms for acidified copper sulfate solutions containing thiourea exhibited striking differences in appearance from the voltammograms of the unadulterated solution. Relative changes in the curves with temperature and additive concentration variations were also more pronounced than in the cases of chloride, glue or "Separan". Solutions containing 10 mg/l of thioureau exhibited a current peak during the cathodic sweep at approximately +0.190 v versus the standard hydrogen electrode and the current at these peaks was higher than the current obtained from an unadulterated solution at the same value of overpotential. At 50° and 60° C., a current peak was also noted on the anodic sweep but the peak was shifted in a slightly more anodic direction as compared to the cathodic peak. When the thiourea concentration was increased above 25 mg/l, an extensive current plateau was obtained during the cathodic sweep and persisted to an overpotential of approximately −300 mv. Increase of the electrolytic solution temperature increased the maximum current in the current peak obtained in 10 mg/l thiourea solutions and increased the plateau current in solutions containing thiourea concentrations above 25 mg/l. At constant temperature, increasing the thiourea concentration generally increased polarizaton and thus decreased the limiting (plateau) current.

The distinct current maximums observed on the voltammograms for solutions containing 10 mg/l thiourea were indicative of the occurrence of some type of reduction reaction other than the electrodeposition of copper. It is believed that some type of complex film consisting of copper and sulfur forms on the cathode in electrolytic solutions containing thiourea. Scanning-electron photomicrographs further indicate that the electrodeposit obtained from thiourea-containing solutions exhibits a smaller particle size than the deposit from an unadulterated acidified copper sulfate solution, and this size difference may possibly be attributable to the interaction of the deposited copper-sulfur film with the electrogrowth process. The current plateaus obtained with electrolytic solutions containing 25 mg/l or greater thiourea were indicative of a passive film on the cathode. The decrease in the value of the limiting current with increasing thiourea concentration further indicated that the film was probably cathodically adsorbed and the degree of coverage or thickness attained was a function of the amount of thiourea available. The prominent plateau or peak during the anodic sweep which appeared in the same range as the cathodic current peak in all thiourea-containing solutions regardless of concentration or temperature suggested the reformation of a copper-sulfur film which was apparently broken down at approximately −300 mv during the cathodic sweep.

Figure 10:
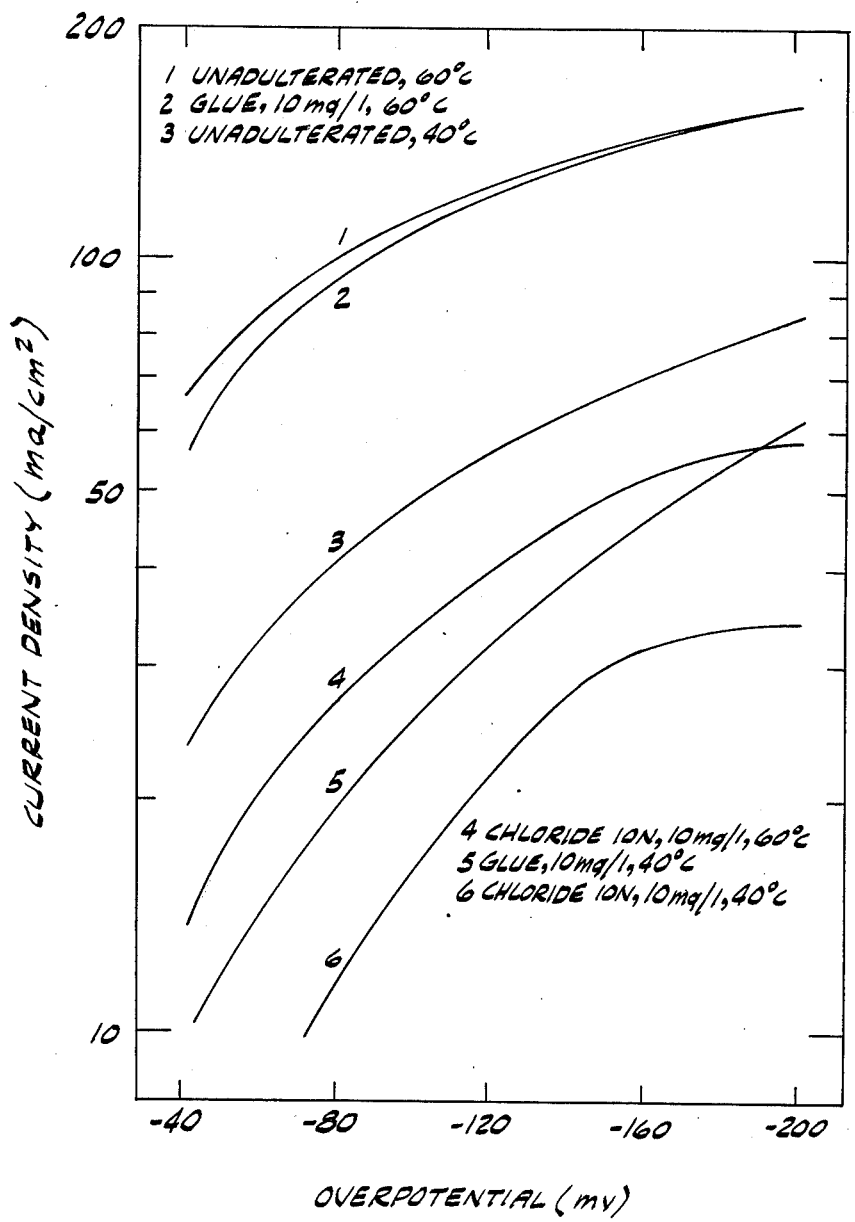
FIG. 10 shows the cathodic current/anodic sweep curves for unadulterated, glue or chloride ion containing acidified copper sulfate electrolytic solution (45 gpl $Cu^{++}$, 200 gpl $H_2SO_4$) at 40° and 60° C. using a copper cathode.
Figure 11:
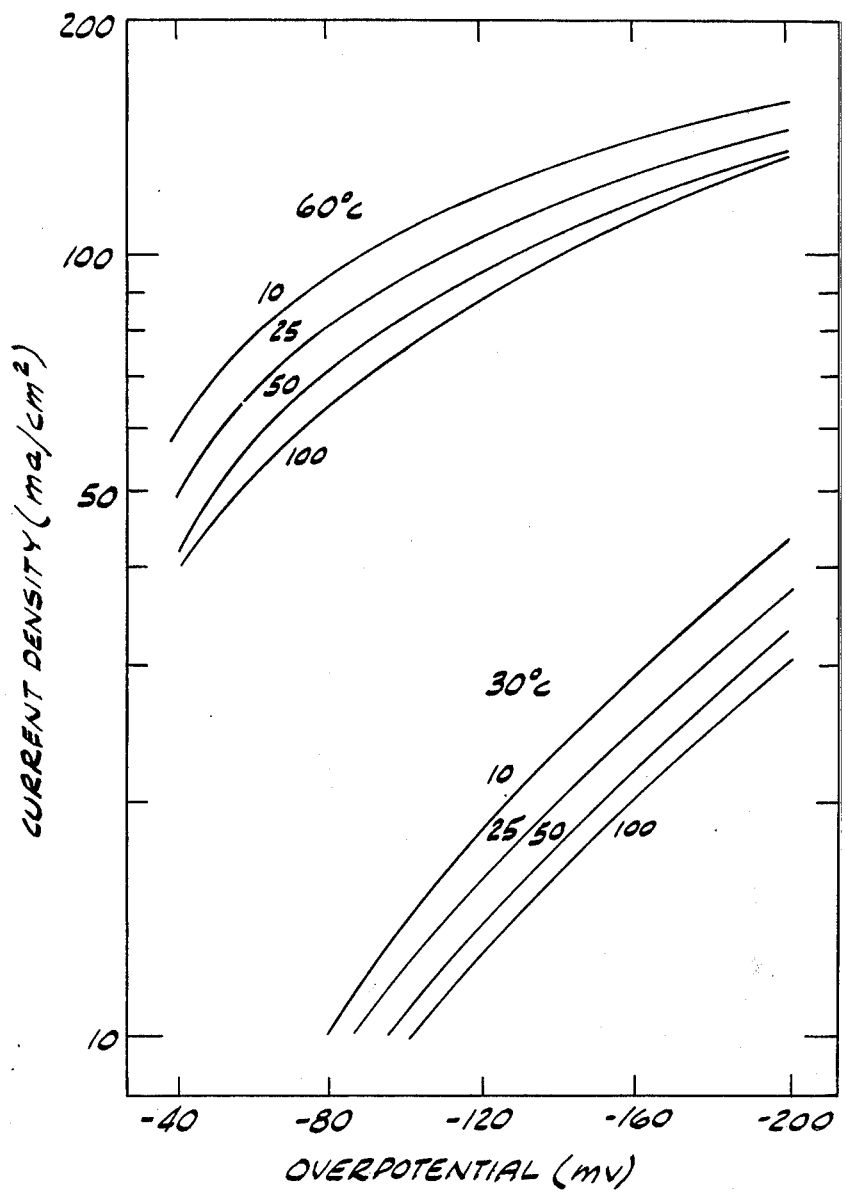
FIG. 11 shows the cathodic current/anodic sweep curves for acidified copper sulfate electrolytic solution (45 gpl $Cu^{++}$, 200 gpl $H_2SO_4$) at 30° and 60° C. containing 10, 25, 50 or 100 mg/l glue using a copper cathode.
Figure 12:
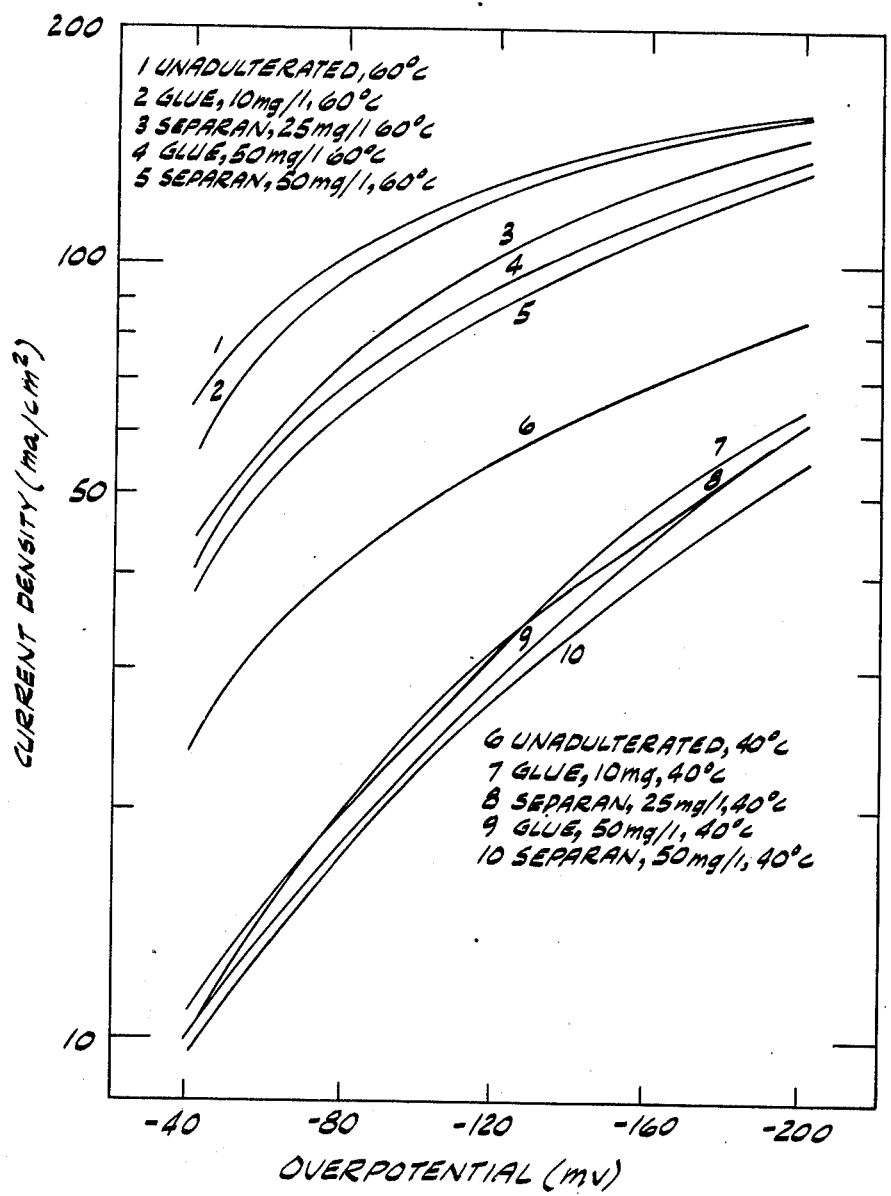
FIG. 12 shows the cathodic current/anodic sweep curves for unadulterated or organic additive containing acidified copper sulfate electrolytic solutions (45 gpl $Cu^{++}$, 200 gpl $H_2SO_4$) at 40° and 60° C. using a copper cathode.
Figure 13:
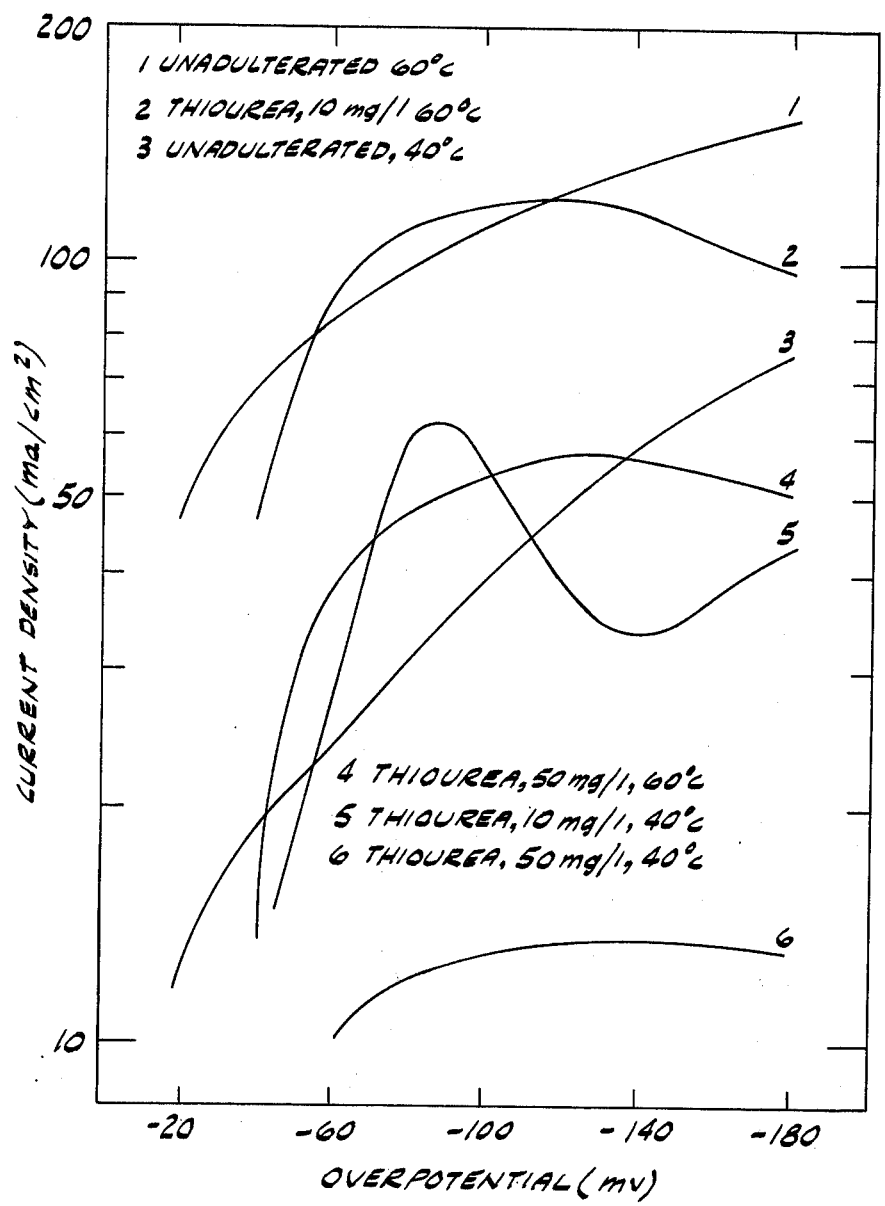
FIG. 13 shows cathodic sweep curves for unadulterated or thiourea containing acidified copper sulfate electrolytic solutions (45 gpl $Cu^{++}$, 200 gpl $H_2SO_4$) at 40° and 60° C. using a copper cathode.

Shown in FIG. 10 are anodic sweep curves at 40° and 60° C. for unadulterated acidified copper sulfate solution and solutions containing glue or chloride ion. FIG. 11 compares anodic sweep curves for acidified copper sulfate solutions containing various concentrations of glue at 30° and 60° C. FIG. 12 shows the anodic sweep curves for unadulterated electrolytic solution at 40° and 60° C. together with curves obtained at the same temperatures for various concentrations of glue and "Separan", while FIG. 13 sets forth the cathodic sweep curves for the unadulterated solution and for solutions containing various concentrations of thiourea at 40° and 60° C. temperatures.

Scanning electron photomicrographs were taken of copper electrodeposits from an unadulterated electrolytic solution and one containing 20 mg/l thiourea. The deposits photomicrographed were produced by cathodically scanning to −135 mv overpotential and immediately removing the electrode from the solution for examination. The electrodeposit from the thiourea solution exhibited a smaller particle size than the deposit from an unadulterated solution, a difference which may be attributable to the interaction of a copper-sulfur film with the electrogrowth process.

EXAMPLE 6

Cyclic voltammograms and copper electrodeposits were obtained on various acidified copper sulfate solutions using the apparatus and method generally described in Example 5 except that the cathode was prepared from high purity titanium rod stock and had an exposed surface area of 0.5 cm$^2$. As in Example 5, runs were conducted with various concentrations of chloride ion, glue, "Separan" and thiourea. The unadulterated electrolytic solution was also run.

Figure 14:
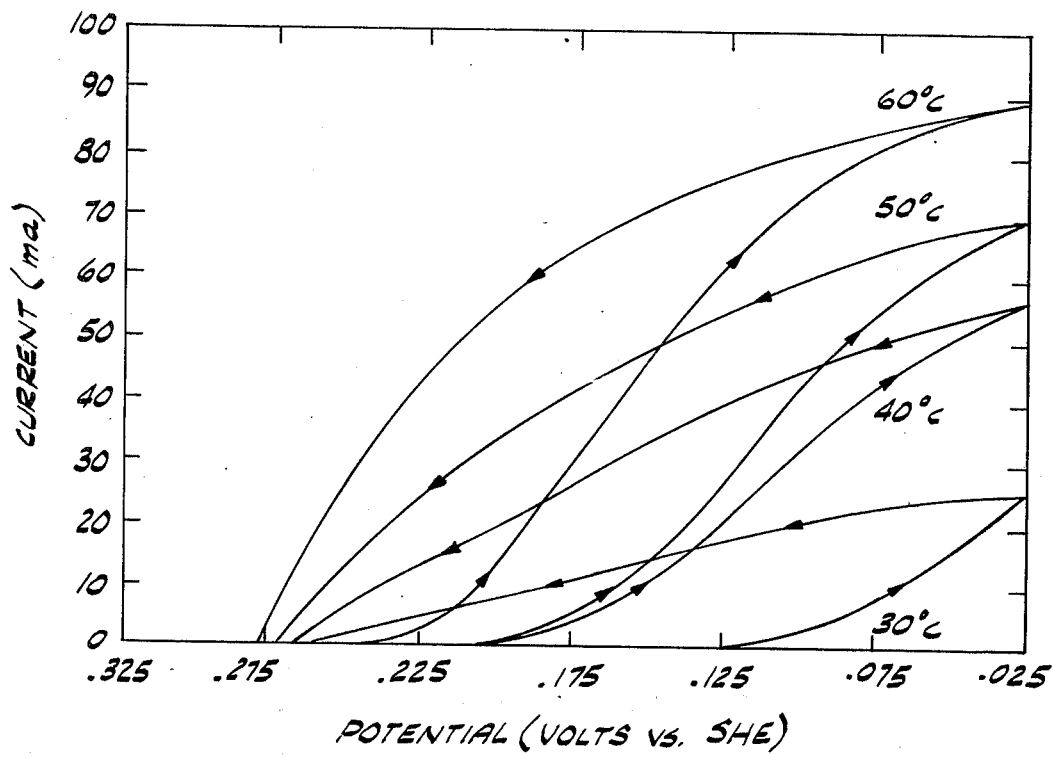
FIG. 14 shows a series of cyclic voltammograms for acidified copper sulfate electrolyte (45 gpl $Cu^{++}$, 200 gpl $H_2SO_4$) at 30°, 40°, 50° and 60° C. using a titanium cathode.

In taking the voltammograms for the unadulterated solution, the initial potential was +0.325 v versus the standard hydrogen electrode and the potential was scanned cathodically to an overpotential of −300 mv, reversed and anodically scanned back to the original starting potential. Set forth in FIG. 14 are the voltammograms for the unadulterated solution at four different temperatures. These curves indicate that increasing solution temperature depolarizes the deposition process. Additionally, the anodic sweeps always produced higher currents than the cathodic sweeps.

Figure 15:
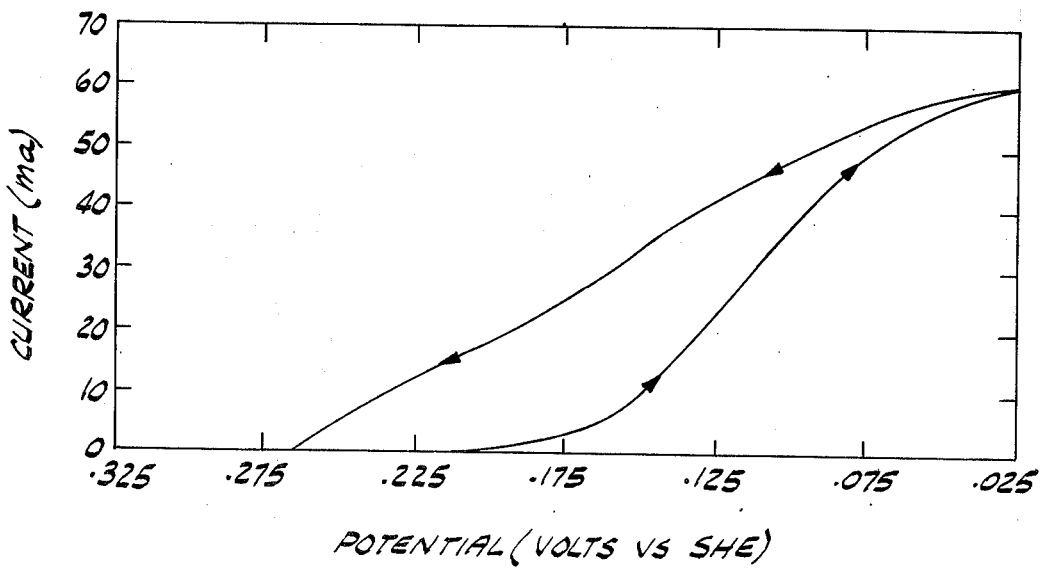
FIG. 15 shows a cyclic voltammogram for acidified copper sulfate electrolytic solution (45 gpl $Cu^{++}$, 200 gpl $H_2SO_4$) at 40° C. containing 25 mg/l chloride ion using a titanium cathode.
Figure 16:
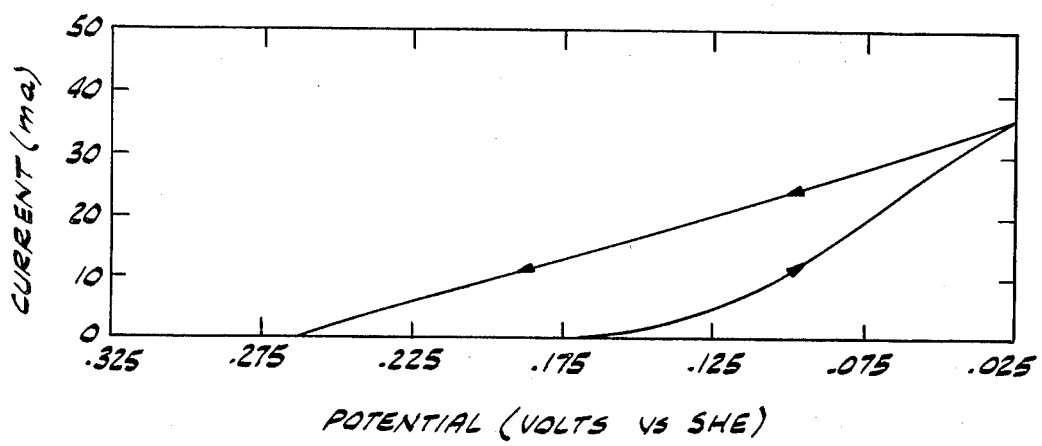
FIG. 16 is a cyclic voltammogram for acidified copper sulfate electrolytic solution (45 gpl $Cu^{++}$, 200 gpl $H_2SO_4$) at 40° C. containing 50 mg/l glue using a titanium cathode.
Figure 17:
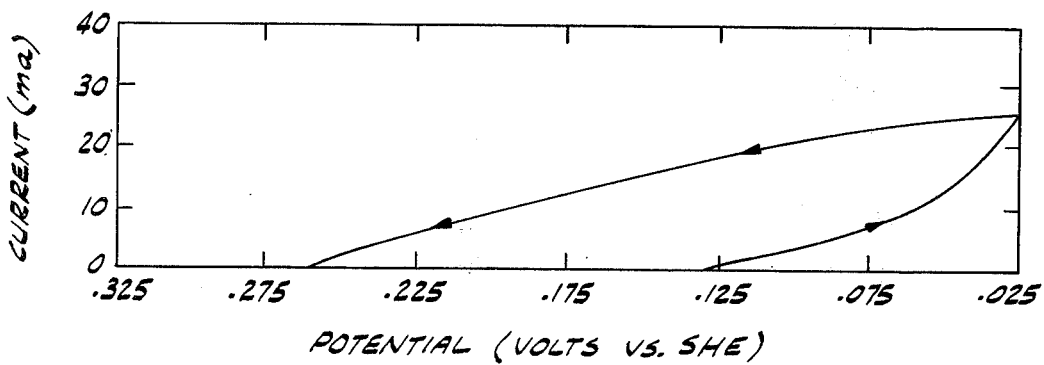
FIG. 17 is a cyclic voltammogram for acidified copper sulfate electrolytic solution (45 gpl $Cu^{++}$, 200 gpl $H_2SO_4$) at 40° C. containing 50 mg/l "Separan" (Dow NP-10) using a titanium cathode.

The maximum voltage of −300 mv overpotential was also utilized in the voltammograms for solutions containing various impurities. Typical voltammograms for solutions containing chloride ion, glue and "Separan" are set forth in FIGS. 15, 16 and 17, respectively. It may be noted that the shapes of these voltammograms are generally similar, but distinguishing variations occur in the cathodic sweep portion which provide an indication of the nature and concentration of impurity present. Moreover, at constant potential the impurities could generally be differentiated by their effect on the degree of polarization, with the current density obtained at a given potential varying as follows: (a) at 40° C.: chloride ion > unadulterated solution > glue > "Separan"; (b) at 60° C.: thiourea > "Separan" > unadulterated solutuion > chloride.

Figure 18:
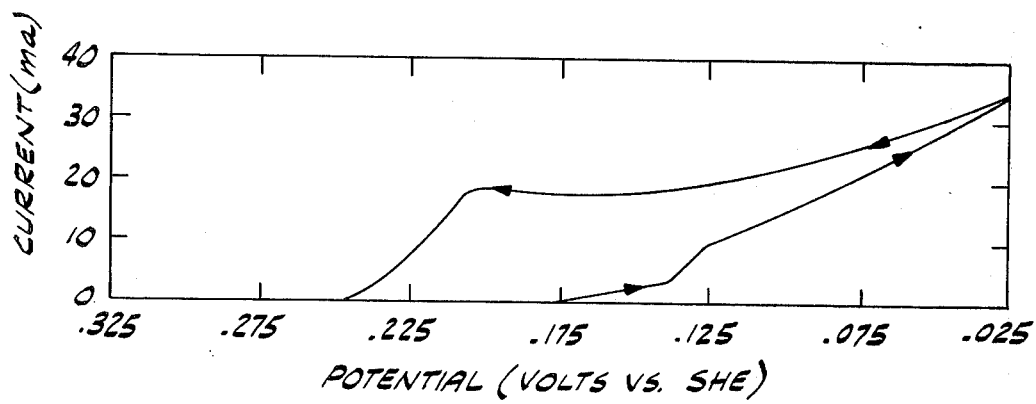
FIG. 18 is a cyclic voltammogram for acidified copper sulfate electrolytic solution (45 gpl $Cu^{++}$, 200 gpl $H_2SO_4$) at 40° C. containing 25 mg/l thiourea using a titanium cathode.
Figure 19:
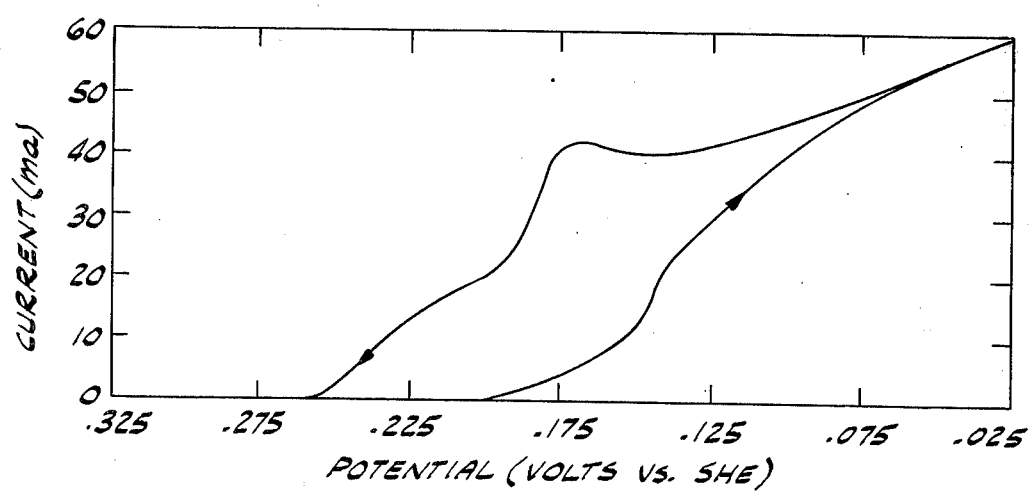
FIG. 19 is a cyclic voltammogram for acidified copper sulfate electrolytic solution (45 gpl $Cu^{++}$, 200 gpl $H_2SO_4$) at 50° C. containing 50 mg/l thiourea using a titanium cathode.

Two types of voltammograms generated for thiourea additions are set forth in FIGS. 18 and 19. These voltammograms show definitive inflection points, current peaks and current plateaus, characteristics which were probably due to the interaction of a copper-sulfur film with the metal deposition process. Increases in electrolytic solution temperature produced more prominent inflection points. Also at high electrolytic solution temperatures, it was noted that over specified range of potential the anodic sweep current densities decreased with increasing thiourea content in the electrolytic solution. In all cases, the anodic sweeps produced higher cathodic currents than the cathodic sweeps and a small current peak was sometimes present before an abrupt decrease in current on the anodic sweep.

Scanning electron photomicrographs indicated that, as the degree of polarization on the titanium cathode increased, the electrodeposit facet size decreased but without any apparent effect on the copper crystal electrode coverage. Thus, the additives which affected polarization behavior also directly influenced the crystal growth but not the initial degree of of nucleation. As reflected in the relative degree of polarization, the "Separan"-containing solution at 40° C. produced crystals with an extremely fine facet size, while the chloride ion-containing solution produce cubic or pyramidal crystals with the largest facet size. At 60° C. the greatest degree of polarization was observed with thiourea and at this temperature the thiourea-containing solution produced the finest facet size, while the chloride ion-containing solution again produced crystals with the largest facet size.

The polarization curves for glue solutions were intermediate those of the unadulterated and "Separan" solutions, and, therefore, the facet size from glue-containing solutions might have been expected to be smaller than those for the unadulterated solution. However, at both 40° and 60° C., the glue solution produced crystals with a larger facet size than the unadulterated solution. Glue-type electrodeposits were identifiable morphologically but the polarization curve did not follow the facet size polarization relationship of the other solutions.

Deposits made with additive combinations were also examined by scanning electron microscopy to determine which additive, if either, would predominate. A consistent relationship was found at high temperature indicating that the morphology of the copper deposit was related to the polarization curve. As polarization increase, the angularity of the facets decreased.

The electrolytic solution temperature had a noticeable influence on the morphology of the copper electrodeposits for both single additions and combinations of additions. These morphological changes were probably due to variations in the activity and stability of the addition agent. Where cyclic voltammetry is used for electrolytic solution evaluation, therefore, it is desirable to obtain known relationships between solution composition and morphology over a range of temperatures. This temperature range should be determined by experimentation so that the change noted in the structure from temperature cycling can be used to indicate additive stability, possible degree of degradation, and possible changes in the relative electrochemical activity of the various additives.

As indicated above, an important application of the method of the invention is in go/no-go type testing for the determination of whether electrolytic solutions or electrodes are suitable for use in an electrolytic system. An electrolytic solution quality standard can be established, and solutions whose voltammograms do not meet this standard may be rejected. In this regard, a particular advantage of the method is that the active concentration of organic contaminants such as protein glue may be estimated to a reasonable degree of accuracy. In the past it has been all but impossible to quantitatively determine this type of parameter, which has made cathode deposit control dfficult at best.

As further noted above, the use of the method of this invention is not limited to go/no-go testing, but may further be used as a process control tool which allows systematic corrective adjustments to be made to the electrolytic solutions used in electrolytic systems. The method of the invention has further utility in evaluating new electrolytic processes. A series of voltammograms taken with the same electrode can be used in determining the effect of impurities and/or additives in the electrolytic solution, while a series of voltammograms taken with a standard electrolytic solution can be utilized in selecting the optimum electrode characteristics. In either a new or existing process, moreover, potential process modifications, for example, an increase or a decrease in current density, can be evaluated by the use of cyclic voltammograms.

In evaluation of either new or existing processes, cyclic voltammetry presents the unique advantage of providing useful data on the deposition of a metal on itself, the circumstance under which commercial cells normally operate.

As a result of the number of independent variables to be specified in the taking of cyclic voltammograms, together with the number of different characteristics which can be observed in the voltammetric curve, the method of the invention affords a wide array of analytical tools for discriminating between electrolytic solutions with regard to impurities present, impurities content and performance characteristics. Thus a relatively large number of relationships can be scrutinized for their significance as indicia of electrolytic solution quality. As noted above, for example, a series of voltammograms can be taken at different temperatures and an analysis made on the basis of the effect of temperature on polarization or backsweep slope as a function of various additives and additive content. Similarly, the effect of sweep rate on the voltammetric curve characteristics can be determined as a function of various additives and further valuable process control information provided. Ultimately, this process control tool is used to control decomposition potential, current efficiency, deposit morphology and other operating characteristics which materially affect manufacturing costs, productivity and product quality.

In view of the above, it will be seen that the several objects of the invention are achieved and other advantageous results attained.

As various changes could be made in the above methods without departing from the scope of the invention, it is intended that all matter contained in the above description or shown in the accompany drawings shall be interpreted as illustrative and not in a limiting sense.

What is claimed is:

1. A method for evaluating an unknown electrolytic system comprising an acidic electrolytic solution and electrodes for electrodeposition of metals with respect to determining the performance characteristics of the electrolytic solution, detection of impurities or additives in the electrolytic solution, estimation of the current efficiency characteristics of said system, or determining the performance characteristics of an electrode, the method comprising the steps of:

establishing an electrolytic circuit comprising a sample of the acidic electrolytic solution for said system, two electrodes immersed in said solution and spaced from one another therein, and a variable and reversible voltage source having its output terminals respectively connected to said electrodes;

applying a predetermined initial voltage to one of said electrodes constituting a working electrode;

varying the voltage in the negative direction until a predetermined cathodic current or predetermined maximum voltage sufficient to cause a cathodic reaction is attained at said working electrode thereby causing reduction of metal ions and deposition of metal at said electrode;

reversing the direction of change of voltage and varying the voltage in the positive direction until a predetermined minimum voltage or a predetermined minimum current is attained at said working electrode thereby causing oxidation and redissolution of the metal which had been deposited by said cathodic reaction;

repetitively varying the voltage in the negative direction, reversing it, and varying it in the positive direction through a plurality of cycles until a pseudoequilibrium is reached;

recording the current obtained as a function of voltage for a cycle representative of the pseudoequilibrium; and determining the performance characteristics of the sample solution, the presence of an impurity or additive, the current efficiency, or the working electrode characteristics according to the recorded relationship between current and voltage at pseudoequilibrium.

2. A method as set forth in claim 1 wherein the presence or concentration of an impurity or additive is determined by comparing the current versus voltage function obtained for the unknown system with current versus voltage functions for known systems having known concentrations of impurities or additives and the same electrolyte composition and concentration and the same electrodes as the unknown system.

3. A method as set forth in claim 1 wherein the characteristics of an unknown working electrode are determined by comparing the current versus voltage function for the unknown system with the current versus voltage functions for known systems having the same electrolytic solution as the unknown system.

4. A method as set forth in claim 1 where the current is graphically recorded as a function of voltage on an X-Y grid.

5. A method as set forth in claim 1 wherein at said pseudoequilibrium an anodic current is maintained for a period of time sufficient to redissolve all metal deposited on the working electrode from the electrolytic solution during the application of a cathodic current.

6. A method as set forth in claim 5 wherein the current efficiency is determined by comparing a function of the electrical work done during the cathodic current portion of the cycle with a function of the electrical work done during the anodic current portion of the cycle.

7. A method as set forth in claim 6 wherein the current is graphically recorded as a function of voltage on an X-Y grid and the electrical work during each of the cathodic and anodic current portions of the cycle is determined from the area under the current versus voltage curve during such portions of the cycle.

8. A method as set forth in claim 1 wherein said electrolytic solution is an acidified zinc sulfate electrowinning solution.

9. A method as set forth in claim 1 wherein said electrolytic solution is an acidified copper sulfate electrodeposition solution.

10. A method for the control of a process for the electrodeposition of a metal comprising the steps of:

establishing an electrolytic test circuit comprising a sample of the electrolytic solution for said process, two electrodes immersed in said solution and spaced from one another therein, and a variable and reversible voltage source having its output terminals respectively connected to said electrodes;

applying a predetermined initial voltage to one of said electrodes constituting a working electrode;

varying the voltage in the negative direction until a predetermined cathodic current or a predetermined maximum voltage sufficient to cause a cathodic reaction is attained at said working electrode thereby causing reduction of metal ions and deposition of metal at said electrode;

reversing the direction of change of voltage and varying the voltage in the positive direction until a predetermined minimum voltage or a predetermined minimum current is attained at said working electrode thereby causing oxidation and redissolution of the metal which had been deposited by said cathodic reaction;

repetitively varying said voltage in the negative direction, reversing it, and varying it in the positive direction through a plurality of cycles until a pseudoequilibrium is reached;

recording the current obtained as a function of voltage for a cycle representative of the pseudoequilibrium;

determining the performance characteristics of the electrolytic solution sample, the presence of an impurity or additive, the current efficiency, or the working electrode characteristics according to the recorded relationship between current and voltage; and taking corrective action in said process based on the indicated presence of an impurity, additive, current efficiency, or working electrode characteristics.

11. A process control method as set forth in claim 10 wherein the presence or concentration of an impurity or additive in the electrolytic solution sample is determined by comparing the current versus voltage function obtained for the test circuit with the current versus voltage functions for known systems having known concentrations of impurity or additive and the same electrolyte composition and concentration and the same electrodes as the test circuit.

12. A method as set forth in claim 11 wherein the composition of the electrolytic solution for use in the process is adjusted in response to the detected effect of impurities or additives on the current versus voltage function of the test circuit.

13. A method as set forth in claim 12 wherein alternate solution composition adjustments and cyclic current versus voltage tests are conducted until the current versus voltage function for the test circuit conforms to a specification.

14. A method as set forth in claim 10 wherein the characteristics of the test working electrode are determined by comparing current versus voltage function for the test circuit with the current versus voltage functions for known systems having the same electrolytic solution as the test circuit.

15. A method as set forth in claim 10 wherein the current is graphically recorded as a function of voltage on an X-Y grid.

16. A method as set forth in claim 10 wherein an anodic current is maintained for a period of time sufficient to redissolve all metal deposited on the working electrode from the electrolytic solution during the application of a cathodic current.

17. A method as set forth in claim 16 wherein current efficiency is determined by comparing a function of the electrical work done during the cathodic current portion of the cycle with a function of the electrical work done during the anodic portion of the cycle.

18. A method as set forth in claim 17 wherein the composition of the electrolytic solution is adjusted in response to the current versus voltage function obtained for the test circuit.

19. A method as set forth in claim 18 wherein alternate composition adjustments are made to the electrolytic solution and current versus voltage functions obtained on the adjusted solution until a current versus voltage relationship is obtained which corresponds to a specification.

20. A method as set forth in claim 10 wherein the electrolytic solution for the process is acidic.

* * * * *

REEXAMINATION CERTIFICATE (724th)
United States Patent [19]
O'Keefe

[11] B1 4,146,437
[45] Certificate Issued  Jul. 14, 1987

[54] METHOD FOR EVALUATING A SYSTEM FOR ELECTRODEPOSITION OF METALS

[75] Inventor: Thomas J. O'Keefe, Rolla, Mo.

[73] Assignee: The Curators of the University of Missouri, Columbia, Mo.

Reexamination Request:
No. 90/000,671, Nov. 23, 1984

Reexamination Certificate for:
Patent No.: 4,146,437
Issued: Mar. 27, 1979
Appl. No.: 831,811
Filed: Sep. 9, 1977

Related U.S. Application Data

[63] Continuation of Ser. No. 645,609, Dec. 31, 1975, abandoned.

[51] Int. Cl.⁴ .................................................. G01N 27/46
[52] U.S. Cl. ................................. 204/1 T; 204/14.1; 204/412; 204/434
[58] Field of Search .............. 204/1 T, 400, 434, 52 R, 204/55 R

[56] References Cited

U.S. PATENT DOCUMENTS

| | | | |
|---|---|---|---|
| 2,882,209 | 4/1959 | Brown et al. | 204/52 R |
| 3,691,038 | 9/1972 | Von Roepenace et al. | 204/119 |
| 3,766,024 | 10/1973 | Yamagishi et al. | 204/55 R |
| 3,925,168 | 12/1975 | Costas | 204/52 R |

OTHER PUBLICATIONS

D. M. MacArthur, "A Study of Gold Reduction & Oxidation in Aqueous Solution", *J. Electrochemical Soc. Electrochemical Science and Technology*, Jun., 1972, pp. 672-677.

Willard et al., "Instrumental Methods of Analysis", 1974, pp. 652-653.

Stulkova et al., *Electroanalytical Chemistry & Interfacial Electrochemistry*, (1973), pp. 117-118.

*Primary Examiner*—T. Tung

[57] ABSTRACT

A method is provided for evaluating an unknown electrolytic system comprising an electrolytic solution and electrodes for electrodeposition of metal with respect to determining the performance characteristics of the electrolytic solution, detection of impurities and additives in the electrolytic solution, estimation of the current efficiency characteristics of the system, or determining the performance characteristics of an electrode. An electrolytic circuit is established comprising a sample of the electrolytic solution for the system, two electrodes immersed in the solution and spaced from one another therein, and a variable and reversible voltage source having its output terminals respectively connected to the electrodes. A predetermined initial voltage is applied to one of the electrodes constituting a working electrode. Thereafter, the voltage is varied in the negative direction until a predetermined cathodic current or predetermined maximum voltage sufficient to cause a cathodic reaction is attained at the working electrode. The direction of the voltage change is then reversed and the voltage is varied in the positive direction until a predetermined minimum voltage or a predetermined minimum current is attained at the working electrode. This process is repeated through a plurality of cycles and the current obtained is recorded as a function of voltage for a selected cycle. The performance characteristics of the sample solution, the presence of an impurity or additive, the current efficiency, or the working electrode characteristics are determined according to the recorded relationship between current and voltage. The method is useful in the control of electrodeposition processes since it not only provides a basis for evaluating electrolytic solutions and electrodes but further constitutes an analytical tool adapted for determining compositional adjustments necessary for optimum cell performance.

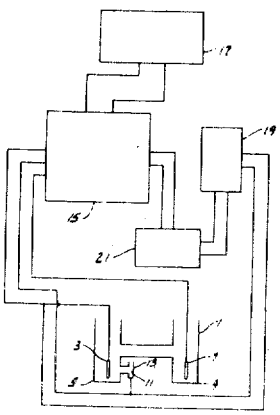

SCHEMATIC FOR APPARATUS SET-UP

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2–20 are cancelled.

Claim 1 is determined to be patentable as amended.

1. A method for evaluating an unknown electrolytic system comprising an acidic electrolytic solution and electrodes for electrodeposition of metals with respect to determining the performance characteristics of [the electrolytic solution, detection of impurities or additives in the electrolytic solution, estimation of the current efficiency characteristics of said system, or determining the performance characteristics of] an *unknown working* electrode, the method comprising the steps of:

establishing an electrolytic circuit comprising a sample of the acidic electrolytic solution for said system, two electrodes immersed in said solution and spaced from one another therein, and a variable and reversible voltage source having its output terminals respectively connected to said electrodes;

applying a predetermined initial voltage to one of said electrodes constituting [a] *an unknown* working electrode;

varying the voltage in the negative direction until a predetermined cathodic current or predetermined maximum voltage sufficient to cause a cathodic reaction is attained at said working electrode thereby causing reduction of metal ions and deposition of metal at said electrode;

reversing the direction of change of voltage and varying the voltage in the positive direction until a predetermined minimum voltage or a predetermined minimum current is attained at said working electrode thereby causing oxidation and redissolution of the metal which had been deposited by said cathodic reaction;

repetitively varying the voltage in the negative direction, reversing it, and varying it in the positive direction through a plurality of cycles until a pseudoequilibrium is reached;

recording the current obtained as a function of voltage for a cycle representative of the pseudoequilibrium, and determining the [performance characteristics of the sample solution, the presence of an impurity or additive, the current efficiency, or the] working electrode characteristics according to the recorded relationship between current and voltage at pseudoequilibrium *by comparing the current versus voltage function for the unknown system with the current versus voltage functions for known systems having the same electrolytic solution as the unknown system.*

* * * * *